(12) United States Patent
Leonhardt

(10) Patent No.: US 11,446,488 B2
(45) Date of Patent: Sep. 20, 2022

(54) KIDNEY TREATMENT

(71) Applicant: Leonhardt Ventures LLC, Mission Viejo, CA (US)

(72) Inventor: Howard J. Leonhardt, Mission Viejo, CA (US)

(73) Assignee: Leonhardt Ventures LLC, Mission Viejo, CA (US)

( * ) Notice: Subject to any disclaimer, the term of this patent is extended or adjusted under 35 U.S.C. 154(b) by 326 days.

(21) Appl. No.: 16/799,694

(22) Filed: Feb. 24, 2020

(65) Prior Publication Data

US 2020/0289820 A1 Sep. 17, 2020

Related U.S. Application Data

(63) Continuation-in-part of application No. 16/352,756, filed on Mar. 13, 2019.

(51) Int. Cl.
*A61N 1/36* (2006.01)
*A61N 1/04* (2006.01)
*A61N 1/32* (2006.01)

(52) U.S. Cl.
CPC ....... *A61N 1/36007* (2013.01); *A61N 1/0452* (2013.01); *A61N 1/0492* (2013.01); *A61N 1/326* (2013.01); *A61N 1/36003* (2013.01)

(58) Field of Classification Search
CPC .............. A61N 1/36007; A61N 1/0452; A61N 1/0492; A61N 1/326; A61N 1/36003; A61N 1/0408; A61N 1/36034
See application file for complete search history.

(56) References Cited

U.S. PATENT DOCUMENTS

| | | | |
|---|---|---|---|
| D263,073 S | 2/1982 | Jonkers et al. |
| D273,893 S | 5/1984 | Weitzman |
| 4,622,952 A | 11/1986 | Gordon |
| 4,976,733 A | 12/1990 | Girardot |
| 5,211,622 A | 5/1993 | Liboff et al. |
| 5,295,958 A | 3/1994 | Shturman |
| 5,543,318 A | 8/1996 | Smith et al. |
| 5,693,029 A | 12/1997 | Leonhardt |
| 5,713,917 A | 2/1998 | Leonhardt et al. |
| 5,725,377 A | 3/1998 | Lemler et al. |
| 5,817,139 A | 10/1998 | Kasano |
| 5,957,949 A | 9/1999 | Leonhardt et al. |

(Continued)

FOREIGN PATENT DOCUMENTS

| | | |
|---|---|---|
| CA | 2685161 A1 | 10/2007 |
| EP | 0603451 A1 | 6/1994 |

(Continued)

OTHER PUBLICATIONS

Alves et al. "A mesenchymal stromal cell gene signature for donor age" PLoS One. 2012;7(8):e42908. doi: 10.1371/journal.pone.0042908. Epub Aug. 23, 2012. PMID: 22927939; PMCID: PMC3426516.

(Continued)

*Primary Examiner* — Eugene T Wu
(74) *Attorney, Agent, or Firm* — TraskBritt

(57) ABSTRACT

Described is a low voltage, pulsed electrical stimulation device for controlling expression of klotho, a useful protein, by tissues. Also described are methods of enhancing expression of klotho in cells and treating a subject's kidneys.

18 Claims, 12 Drawing Sheets

(56) References Cited

U.S. PATENT DOCUMENTS

| | | |
|---|---|---|
| 6,344,052 B1 | 2/2002 | Greenan et al. |
| 6,618,625 B2 | 9/2003 | Silverstone |
| 6,957,106 B2 | 10/2005 | Schuler et al. |
| 6,988,004 B2 | 1/2006 | Kanno et al. |
| 7,029,276 B2 | 4/2006 | Mao |
| 7,136,699 B2 | 11/2006 | Palti |
| 7,341,062 B2 | 3/2008 | Chachques et al. |
| 7,483,749 B2 | 1/2009 | Leonhardt et al. |
| 7,686,799 B2 | 3/2010 | Leonhardt et al. |
| 7,881,784 B2 | 2/2011 | Pasricha et al. |
| 8,041,428 B2 | 10/2011 | Errico et al. |
| 8,133,267 B2 | 3/2012 | Leonhardt et al. |
| 8,166,976 B2 | 5/2012 | Webster et al. |
| 8,226,407 B2 | 7/2012 | Hanewinkel et al. |
| 8,465,533 B2 | 6/2013 | Palti |
| 8,534,289 B2 | 9/2013 | Hernandez |
| 8,639,361 B2 | 1/2014 | Nathanson |
| 8,646,455 B2 | 2/2014 | Webster et al. |
| 8,656,930 B2 | 2/2014 | Schuler et al. |
| 8,660,669 B2 | 2/2014 | Nemeh et al. |
| 8,738,144 B2 | 5/2014 | Schneider |
| 8,909,346 B2 | 12/2014 | Chalmers |
| 8,945,104 B2 | 2/2015 | Boone et al. |
| 9,032,964 B2 | 5/2015 | Schuler et al. |
| 9,173,811 B2 | 11/2015 | Greiner et al. |
| 9,533,170 B2 | 1/2017 | Dye et al. |
| 9,545,331 B2 | 1/2017 | Ingemarsson-Matzen |
| D778,449 S | 2/2017 | Ingemarsson-Matzen |
| 9,656,096 B2 | 5/2017 | Pilla |
| 9,662,184 B2 | 5/2017 | Lowe |
| 9,687,383 B2 | 6/2017 | Ingemarsson-Matzen |
| 9,707,403 B2 | 7/2017 | Schuler |
| 9,855,418 B2 | 1/2018 | Haralambidis |
| 9,987,326 B2 | 6/2018 | Koeffler et al. |
| D832,447 S | 10/2018 | Wiffen |
| 10,543,119 B2 | 1/2020 | Ingemarsson-Matzen |
| D881,399 S | 4/2020 | Ingemarsson-Matzen |
| 10,646,644 B2 | 5/2020 | Leonhardt et al. |
| 10,960,206 B2 | 3/2021 | Leonhardt et al. |
| 11,058,536 B2 | 7/2021 | Huber |
| 11,110,274 B2 | 9/2021 | Leonhardt |
| 2002/0143373 A1 | 10/2002 | Courtnage et al. |
| 2003/0032998 A1 | 2/2003 | Altman |
| 2003/0220556 A1 | 11/2003 | Porat et al. |
| 2004/0010231 A1 | 1/2004 | Leonhardt et al. |
| 2004/0115587 A1 | 6/2004 | Breining et al. |
| 2004/0147906 A1 | 7/2004 | Voyiazis et al. |
| 2004/0236238 A1 | 11/2004 | Schuler et al. |
| 2005/0171578 A1 | 8/2005 | Leonhardt |
| 2006/0030908 A1 | 2/2006 | Powell et al. |
| 2006/0100553 A1 | 5/2006 | Lodin |
| 2007/0123758 A1 | 5/2007 | Miesel et al. |
| 2007/0167984 A1 | 7/2007 | Kieval et al. |
| 2007/0190028 A1 | 8/2007 | Qu et al. |
| 2007/0265680 A1 | 11/2007 | Liu et al. |
| 2008/0227046 A1 | 9/2008 | Lowe et al. |
| 2008/0243060 A1 | 10/2008 | Hartmann et al. |
| 2009/0132010 A1 | 5/2009 | Kronberg |
| 2009/0240304 A1 | 9/2009 | Blum et al. |
| 2010/0082027 A1 | 4/2010 | Chalmers |
| 2010/0184183 A1 | 7/2010 | Schussler et al. |
| 2012/0156648 A1 | 6/2012 | Kaufman et al. |
| 2013/0253413 A1 | 9/2013 | Levine et al. |
| 2014/0023983 A1 | 1/2014 | Lowe et al. |
| 2014/0214115 A1 | 7/2014 | Greiner et al. |
| 2014/0214116 A1 | 7/2014 | Peterson et al. |
| 2014/0214124 A1 | 7/2014 | Greiner et al. |
| 2014/0214144 A1 | 7/2014 | Peterson et al. |
| 2014/0228910 A1 | 8/2014 | Schuler et al. |
| 2017/0028184 A1 | 2/2017 | Godden et al. |
| 2017/0036032 A1 | 2/2017 | Schuler et al. |
| 2017/0112983 A1 | 4/2017 | Thorne et al. |
| 2017/0266371 A1 | 9/2017 | Leonhardt et al. |
| 2017/0274206 A1 | 9/2017 | Leonhardt |
| 2018/0043159 A1 | 2/2018 | Hassan et al. |
| 2018/0064935 A1 | 3/2018 | Leonhardt et al. |
| 2018/0071135 A1 | 3/2018 | Ingemarsson-Matzen |
| 2018/0193646 A1* | 7/2018 | Fostick ............ A61N 1/20 |
| 2019/0015661 A1 | 1/2019 | Leonhardt et al. |
| 2019/0022389 A1 | 1/2019 | Leonhardt |
| 2019/0022396 A1 | 1/2019 | Leonhardt |
| 2019/0125932 A1 | 5/2019 | Leonhardt et al. |
| 2019/0255321 A1 | 8/2019 | Planard-Luong |
| 2019/0290541 A1 | 9/2019 | Greiner et al. |
| 2020/0030136 A1 | 1/2020 | Hernandez |
| 2020/0289826 A1 | 9/2020 | Leonhardt |
| 2020/0324106 A1 | 10/2020 | Leonhardt |
| 2020/0330753 A1 | 10/2020 | Leonhardt et al. |
| 2021/0228870 A1 | 7/2021 | Leonhardt |

FOREIGN PATENT DOCUMENTS

| | | |
|---|---|---|
| JP | 2013-034881 A | 2/2013 |
| KR | 10-2007-0010908 A | 1/2007 |
| KR | 10-0726825 B1 | 6/2007 |
| WO | 92/17118 A1 | 10/1992 |
| WO | 2006/116728 A2 | 11/2006 |
| WO | 2007/146187 A2 | 12/2007 |
| WO | 2008/145724 A1 | 12/2008 |
| WO | 2009/021535 A1 | 2/2009 |
| WO | 2011/016629 A2 | 2/2011 |
| WO | 2016/135295 A1 | 9/2016 |
| WO | 2017/142948 A1 | 8/2017 |

OTHER PUBLICATIONS

Andringa et al. "Role of Hypoxia-Inducible Factors in Acute Kidney Injury" Nephron Clin Pract (Sep. 2014) 127: 70-74; doi.org/10.1159/000363669.

Apel et al. (2010), Effect of locally delivered IGF-1 on nerve regeneration during aging: an experimental study in rats, Muscle & nerve, 41(3), 335-341. doi.org/10.1002/mus.21485.

Ayden et al. "Focusing of electromagnetic waves by a left-handed metamaterial flat lens" Optics Express (Oct. 31, 2005) 13(22):8753-8759.

Bäck et al. "Endogenous Calcification Inhibitors in the Prevention of Vascular Calcification: A Consensus Statement From the COST Action EuroSoftCalcNet" Front. Cardiovasc. Med., 918 Jan. 2019): doi.org/10.3389/fcvm.2018.00196.

Bourdillon et al. "Electromagnetic Brain Stimulation in Patients With Disorders of Consciousness" Front. Neurosci., (Mar. 18, 2019): doi.org/10.3389/fnins.2019.00223.

Bowser et al. "Effects of the activin A-myostatin-follistatin system on aging bone and muscle progenitor cells" Exp Gerontol. Feb. 2013;48(2):290-7. doi: 10.1016/j.exger.2012.11.004. Epub Nov. 21, 2012. PMID: 23178301; PMCID: PMC3678732.

Bre et al. "Prevention of bioprosthetic heart valve calcification: strategies and outcomes". Curr Med Chem. 2014;21(22):2553-64. doi: 10.2174/0929867321666131212151216. PMID: 24358975.

Cai et al. "Intermedin inhibits vascular calcification by increasing the level of matrix ?-carboxyglutamic acid protein", Cardiovascular Research, vol. 85, Issue 4, Mar. 1, 2010, pp. 864-873, doi.org/10.1093/cvr/cvp366.

Caradu et al. "Endogenous Sonic Hedgehog limits inflammation and angiogenesis in the ischaemic skeletal muscle of mice". Cardiovasc Res. Apr. 1, 2018;114(5):759-770. doi: 10.1093/cvr/cvy017. PMID: 29365079.

Carboni et al. "An initial study on the effect of functional electrical stimulation in erectile dysfunction: a randomized controlled trial." Int J Impot Res. Jun. 2018; 30(3):97-101. doi: 10.1038/s41443-018-0024-8. Epub May 22, 2018. PMID: 29785045.

Chen et al. "The Strategy to Prevent and Regress the Vascular Calcification in Dialysis Patients", BioMed Research International, vol. 2017, Article ID 9035193, 11 pages, 2017; doi.org/10.1155/2017/9035193.

Chen et al. "Deficiency in the anti-aging gene Klotho promotes aortic valve fibrosis through AMPKa-mediated activation of RUNX2." Aging Cell vol. 15, 5 (2016): 853-60. doi:10.1111/acel.12494.

(56) References Cited

OTHER PUBLICATIONS

Chen et al. "Regenerative hair waves in aging mice and extra-follicular modulators Follistatin, Dkk1, and Sfrp4" J Invest Dermatol. Aug. 2014;134(8):2086-2096. doi: 10.1038/jid.2014.139. Epub Mar. 11, 2014. PMID: 24618599; PMCID: PMC4102635.
Chen et al. "The Role and Mechanism of a-Klotho in the Calcification of Rat Aortic Vascular Smooth Muscle Cells." BioMed Research International vol. 2015 (2015): 194362. doi:10.1155/2015/194362.
Cheng et al. "The Role of SDF-1/CXCR4/CXCR7 in Neuronal Regeneration after Cerebral Ischemia." Frontiers in Neuroscience vol. 11 590. Oct. 24, 2017, doi:10.3389/fnins.2017.00590.
Chera et al. "Diabetes recovery by age-dependent conversion of pancreatic d-cells into insulin producers." Nature, 2014; DOI: 10.1038/nature13633.
Chu et al. "Mechanical stretch induces hair regeneration through the alternative activation of macrophages." Nature Communications, 10(1), 1524 (2019). doi.org/10.1038/s41467-019-09402-8.
Dalton et al. "New Insights into the Mechanism of Action of Soluble Klotho." Frontiers in endocrinology vol. 8 323. Nov. 17, 2017, doi:10.3389/fendo.2017.00323.
Deng et al. "Effects of SDF-1/CXCR4 on the Repair of Traumatic Brain Injury in Rats by Mediating Bone Marrow Derived Mesenchymal Stem Cells" Cell Mol Neurobiol. Mar. 2018; 38(2):467-477. doi: 10.1007/s10571-017-0490-4. Epub May 8, 2017. Erratum in: Cell Mol Neurobiol. Apr. 2021;41(3):617-618. PMID: 28484859.
Dërmaku-Sopjani et al. "Klotho-Dependent Role of 1,25(OH)2D3 in the Brain" Neurosignals. Mar. 31, 2021;29(1):14-23. doi: 10.33594/000000352. PMID: 33784444.
Dërmaku-Sopjaniet et al. "Significance of the anti-aging protein Klotho" Molecular Membrane Biology, 30:8, 369-385 (Aug. 2013), DOI: 10.3109/09687688.2013.837518.
Diaco et al. "Amniotic fluid-derived stem cells as an effective cell source for transplantation therapy in stroke." Brain Circ 2015;1:119-24.
Dote-Montero et al. "Predictors of Sexual Desire and Sexual Function in Sedentary Middle-Aged Adults: The Role of Lean Mass Index and S-Klotho Plasma Levels. The FIT-AGEING Study." J Sex Med. Apr. 2020;17(4):665-677. doi: 10.1016/j.jsxm.2020.01.016. Epub Feb. 20, 2020. PMID: 32089483.
Drew et al. "Association between Soluble Klotho and Change in Kidney Function: The Health Aging and Body Composition Study" J Am Soc Nephrol Jun. 2017, 28(6):1859-1866; DOI: doi.org/10.1681/ASN.2016080828.
Floege et al. "A New Look at Platelet-Derived Growth Factor in Renal Disease" J Am Soc Nephrol (Jan. 2008), 19(1):12-23; DOI: doi.org/10.1681/ASN.2007050532.
Fu et al. "Loss of Klotho in CKD Breaks One's Heart" J Am Soc Nephrol Oct. 2015, 26 (10) 2305-2307; DOI: https://doi.org/10.1681/ASN.2015020200.
Fukuoka et al. "Hair Regeneration Therapy: Application of Adipose-Derived Stem Cells." Current Stem Cell Research & Therapy vol. 12,7 (2017): 531-534. doi: 10.2174/1574888X12666170522114307.
Garcia et al. "1,25(OH)2vitamin D3 stimulates myogenic differentiation by inhibiting cell proliferation and modulating the expression of promyogenic growth factors and myostatin in C2C12 skeletal muscle cells" Endocrinology. Aug. 2011;152(8):2976-86. doi: 10.1210/en.2011-0159. Epub Jun. 14, 2011. PMID: 21673099; PMCID: PMC3138228.
Geribaldi-Doldán et al. "Protein Kinase C: Targets to Regenerate Brain Injuries?" Front. Cell Dev. Biol., Mar. 20, 2019): doi.org/10.3389/fcell.2019.00039.
Ghuman et al. "Biodegradation of ECM hydrogel promotes endogenous brain tissue restoration in a rat model of stroke". Acta Biomater. Oct. 15, 2018;80:66-84. doi: 10.1016/j.actbio.2018.09.020. Epub Sep. 16, 2018. PMID: 30232030; PMCID: PMC6217851.
Golembiewska et al. "The Role of Klotho Protein in Chronic Kidney Disease: Studies in Animals and Humans" Current Protein & Peptide Science vol. 17, Issue 8, 2016; DOI: 10.2174/1389203717666160526123646.

Grange et al. "Urinary Extracellular Vesicles Carrying Klotho Improve the Recovery of Renal Function in an Acute Tubular Injury Mode" Molecular Therapy vol. 28 No. 2 490-502 (Feb. 2020) (with Supplemental Information) https://doi.org/10.1016/j.ymthe.2019.11.013.
Gutierrez et al. "a-Klotho and Kidney Function Decline: An Important Step Forward in Understanding the Link Between Mineral Metabolism and Kidney Disease Progression" Am J Kidney Dis. (Jun. 2013) 61 (6):855-857.
Guyot et al. "Pancreatic nerve electrostimulation inhibits recent-onset autoimmune diabetes". Nat Biotechnol 37, 1446-1451 (2019): doi.org/10.1038/s41587-019-0295-8.
Hasegawa et al. "Recent advances in renal regeneration." FI000Research vol. 8 F1000 Faculty Rev-216. Feb. 25, 2019, doi:10.12688/f1000research.17127.1.
Hoyer et al. "Electroconvulsive therapy enhances the anti-ageing hormone Klotho in the cerebrospinal fluid of geriatric patients with major depression." Eur Neuropsychopharmacol. Mar. 2018;28(3):428-435. doi:10.1016/j.euroneuro.2017.12.012. Epub Dec. 20, 2017. PMID: 29274997.
Hu et al. "Recombinant a-Klotho may be prophylactic and therapeutic for acute to chronic kidney disease progression and uremic cardiomyopathy" Kidney International Basic Research vol. 91, Issue 5, P1104-1114 (Jan. 2017); DOI:https://doi .org/10.1016/j.kint.2016.10.034.
Hu et al. "Renal and extrarenal actions of Klotho." Seminars In Nephrology vol. 33,2 (2013): 118-29. doi:10.1016/j.semnephrol.2012.12.013.
Hu et al. "Secreted klotho and chronic kidney disease" Advances in Experimental Medicine and Biology, Jan. 1, 2012, 728:126-157; DOI: 10.1007/978-1-4614-0887-1_9.
Jayaraj et al. "Neuroinflammation: friend and foe for ischemic stroke". J Neuroinflammation 16, 142 (2019): doi.org/10.1186/s12974-019-1516-2.
Joo et al. "Various Wavelengths of Light-Emitting Diode Light Regulate the Proliferation of Human Dermal Papilla Cells and Hair Follicles via Wnt/ß-Catenin and the Extracellular Signal-Regulated Kinase Pathways." Annals of Dermatology vol. 29,6 (2017): 747-754. doi:10.5021/ad.2017.29.6.747.
Jorge et al. "Klotho deficiency aggravates sepsis-related multiple organ dysfunction" Am J Physiol Renal Physiol 316: F438-F448, (Dec. 5, 2018); doi:10.1152/ajprenal.00625.2017.
Kim et al. "Wnt/ß-catenin and ERK pathway activation: A possible mechanism of photobiomodulation therapy with light-emitting diodes that regulate the proliferation of human outer root sheath cells." Lasers Surg Med. Dec. 2017;49(10):940-947. doi: 10.1002/lsm.22736. Epub Sep. 25, 2017. PMID: 28944964.
Kinney et al. "High intensity focused electromagnetic therapy evaluated by magnetic resonance imaging: Safety and efficacy study of a dual tissue effect based non-invasive abdominal body shaping." Lasers Surg Med. Jan. 2019;51(1):40-46. doi: 10.1002/lsm.23024. Epub Oct. 10, 2018. PMID: 30302767; PMCID: PMC6585690.
Kuro-O "The Klotho proteins in health and disease" Nat Rev Nephrol 15, 27-44 (Nov. 19, 2018); doi.org/10.1038/s41581-018-0078-3.
Lang et al. "Therapeutic Interference with Vascular Calcification—Lessons From Klotho-Hypomorphic Mice and Beyond" Front. Endocrinol. (May 2018): doi.org/10.3389/fendo.2018.00207.
Lee et al. "Klotho ameliorates diabetic nephropathy via LKB1-AMPK-PGC1a-mediated renal mitochondrial protection" Biochemical and Biophysical Research Communications vol. 534, Jan. 1, 2021, pp. 1040-1046.
Lei "Mechanisms and Reversal Of Elastin Specific Medial Arterial Calcification." (2014). All Dissertations. 1307; tigerprints.clemson.edu/all_dissertations/1307/.
Lei et al. "Efficacy of reversal of aortic calcification by chelating agents." Calcified Tissue International vol. 93,5 (2013): 426-35. doi:10.1007/s00223-013-9780-0.
Leibrock et al. "NH4Cl Treatment Prevents Tissue Calcification in Klotho Deficiency" Journal of the American Society of Nephrology, Oct. 2015, 26 (10) 2423-2433.

(56) References Cited

OTHER PUBLICATIONS

Leon et al. "Peripheral Elevation of a Klotho Fragment Enhances Brain Function and Resilience in Young, Aging, and a-Synuclein Transgenic Mice" Cell Reports vol. 20, Issue 6, Aug. 6, 2017, pp. 1360-1371.

Li et al. "GDF10 is a signal for axonal sprouting and functional recovery after stroke" Nat Neurosci 2015; Epub Oct. 15, 2015.

Li et al. "Hair Growth Promotion Activity and Its Mechanism of Polygonum multiflorum." Evid Based Complement Alternat Med. 2015;2015:517901. doi: 10.1155/2015/517901. Epub Jul. 30, 2015. PMID: 26294926; PMCID: PMC4534627.

Lim et al. "a-Klotho Expression in Human Tissues." The Journal Of Clinical Endocrinology And Metabolism vol. 100, 10 (2015): E1308-18. doi:10.1210/jc.2015-1800.

Lim et al. "Klotho: A Major Shareholder in Vascular Aging Enterprises" Int. J. Mol. Sci. 2019, 20(18), 4637; doi.org/10.3390/ijms20184637.

Liu et al. "Stem cell competition orchestrates skin homeostasis and ageing". Nature 568, 344-350 (2019); doi.org/10.1038/S41586-019-1085-7.

Lu et al. "Klotho/FGF23 Axis in Chronic Kidney Disease and Cardiovascular Disease" Kidney Dis (Jul. 2017) 3:15-23; doi.org/10.1159/000452880.

Malyshevskaya et al. "Role of Electrical Activity in Horizontal Axon Growth in the Developing Cortex: A Time-Lapse Study Using Optogenetic Stimulation" Plos One (2013): doi.org/10.1371/journal.pone.0082954.

Martín-González et al. "Soluble a-Klotho in Liver Cirrhosis and Alcoholism, Alcohol and Alcoholism", vol. 54, Issue 3, May 2019, pp. 204-208.

Martín-Núñez et al. "Implications of Klotho in vascular health and disease" World J Cardiol. Dec. 26, 2014; 6(12):1262-1269.

Martinez-Redondo et al. "aKLOTHO and sTGFßR2 treatment counteract the osteoarthritic phenotype developed in a rat model". Protein Cell 11, 219-226 (2020): doi.org/10.1007/s13238-019-00685-7.

Mir et al. "IGF-1 mediated Neurogenesis Involves a Novel RIT1/Akt/Sox2 Cascade." Sci Rep 7, 3283 (2017):doi.org/10.1038/s41598-017-03641-9.

Missoum et al. "Recent Updates on Mesenchymal Stem Cell Based Therapy for Acute Renal Failure" Curr Urol 2019;13:189-199; DOI: 10.1159/000499272.

Mitani et al. "In Vivo klotho Gene Transfer Ameliorates Angiotensin II-Induced Renal Damage" Hypertension (Apr. 2002) 39:838-843; https://doi.org/10.1161/01.HYP.0000013734.33441.EA.

Morales-García et al. "The alkaloids of Banisteriopsis caapi, the plant source of the Amazonian hallucinogen Ayahuasca, stimulate adult neurogenesis in vitro". Sci Rep 7, 5309 (2017): doi.org/10.1038/s41598-017-05407-9.

Mostafidi et al. "Serum Klotho Levels in Trained Athletes", Nephro-Urol Mon. (Jan. 2016); 8(1):e30245. doi:10.5812/numonthly.30245.

Nakamura et al. "Eicosapentaenoic acid prevents arterial calcification in klotho mutant mice." PLoS One. Aug. 3, 2017;12(8):e0181009. doi: 10.1371/journal.pone.0181009. PMID: 28771600; PMCID: PMC5542469.

Negaresh et al. "The effect of resistance training on quadriceps muscle volume and some growth factors in elderly and young men" Adv Gerontol. 2017;30(6):880-887. PMID: 29608833.

Nih et al. "Dual-function injectable angiogenic biomaterial for the repair of brain tissue following stroke". Nature Mater 17, 642-651 (2018): doi.org/10.1038/s41563-018-0083-8.

Noguchi et al. "Alteration of skin wound healing in keratinocyte-specific mediator complex subunit 1 null mice" PLoS One. Aug. 14, 2014;9(8):e102271. doi: 10.1371/journal.pone.0102271. PMID: 25122137; PMCID: PMC4133190.

Nowak et al. "Prognostic Value and Link to Atrial Fibrillation of Soluble Klotho and FGF23 in Hemodialysis Patients" PLoS One. Jul. 3, 2014;9(7):e100688. doi: 10.1371/journal.pone.0100688.

O'Neill et al. "Recent progress in the treatment of vascular calcification." Kidney International vol. 78,12 (2010):1232-9. doi:10.1038/ki.2010.334.

Pai et al. "Endogenous Gradients of Resting Potential Instructively Pattern Embryonic Neural Tissue via Notch Signaling and Regulation of Proliferation." Journal of Neuroscience, 2015; 35 (10): 4366 DOI: 10.1523/JNEUROSCI.1877-14.2015.

Papaioannou et al. "Sonic Hedgehog signaling limits atopic dermatitis via Gli2-driven immune regulation" J Clin Invest. 2019; 129(8):3153-3170; doi.org/10.1172/JCI125170.

Paroni et al. "Klotho Gene and Selective Serotonin Reuptake Inhibitors: Response to Treatment in Late-Life Major Depressive Disorder". Mol Neurobiol. Mar. 2017;54(2):1340-1351. doi: 10.1007/s12035-016-9711-y. Epub Feb. 3, 2016. PMID: 26843110.

Pastor et al. "Treating Systemic Klotho Deficiency" Am J Nephrol (Apr. 2019) 49:410-412; doi.org/10.1159/000499864.

Prather et al. "Longevity factor klotho and chronic psychological stress". Translational Psychiatry, 2015; 5 (6):e585 DOI: 10.1038/tp.2015.81.

Prud'Homme et al. "The anti-aging protein Klotho is induced by GABA therapy and exerts protective and stimulatory effects on pancreatic beta cells." Biochem Biophys Res Commun. Dec. 2, 2017;493(4):1542-1547. doi: 10.1016/j.bbrc.2017.10.029. Epub Oct. 6, 2017. PMID: 28993191.

Qi et al. "Enhancement of neural stem cell survival, proliferation and differentiation by IGF-1 delivery in graphene oxide-incorporated PLGA electrospun nanofibrous mats" RSC Adv., 2019,9, 8315-8325.

Rhee et al. "Neural stem cells secrete factors facilitating brain regeneration upon constitutive Raf-Erk activation." Sci Rep 6, 32025 (2016): doi.org/10.1038/srep32025.

Sachdeva et al. "Klotho and the Treatment of Human Malignancies" Cancers 2020, 12, 1665; doi:10.3390/cancers12061665.

Sadagurski et al. "Insulin-like growth factor 1 receptor signaling regulates skin development and inhibits skin keratinocyte differentiation." Molecular and Cellular Biology vol. 26,7 (2006): 2675-87. doi:10.1128/MCB.26.7.2675-2687.2006.

Savastano et al. "Insulin-like Growth Factor-1, Psoriasis, and Inflammation: A Ménage à Trois?" European Journal of Inflammation vol. 9 issue: 3, pp. 277-283 (2011).

Seo et al. "Renal Klotho expression in patients with acute kidney injury is associated with the severity of the injury" The Korean Journal of Internal Medicine (Jul. 2015);30(4):489-495.

Sharma et al. "Insulin demand regulates ß cell number via the unfolded protein response." Journal of Clinical Investigation, 2015; DOI: 10.1172/JCI79264.

Sieg "Mini-review of neural regeneration peptides in brain development." Journal of Stem Cell Research & Therapeutics 1 (2016): DOI: 10.15406/JSRT.2016.01.00025 Corpus ID: 14566389.

Sood et al. "Fetal Brain Extracellular Matrix Boosts Neuronal Network Formation in 3D Bioengineered Model of Cortical Brain Tissue" ACS Biomater. Sci. Eng. 2016, 2, 1, 131-140.

Stief et al. "Functional electromyostimulation of the corpus cavernosum penis—preliminary results of a novel therapeutic option for erectile dysfunction," World J. Urol. (1995) 13:243-247.

Sun et al. "Overexpression of Klotho suppresses liver cancer progression and induces cell apoptosis by negatively regulating wnt/ß-catenin signaling pathway." World Journal of Surgical Oncology vol. 13 307. Oct. 24, 2015, doi:10.1186/S12957-015-0717-0.

Takenaka et al. "[OP.4B.02] Klotho Supplementation Attenuates Blood Pressure and Oxidative Stress in Diabetes" Journal of Hypertension Sep. 2017—vol. 35—Issue—p. e38; doi: 10.1097/01.hjh.0000523076.42214.98.

Takenaka et al. "Klotho Ameliorates Medullary Fibrosis and Pressure Natriuresis in Hypertensive Rat Kidneys." Hypertension (Dallas, Tex. : 1979) vol. 72,5 (Nov. 2018): 1151-1159 doi:10.1161/HYPERTENSIONAHA.118.1117.

Tang-Schomer MD. "3D axon growth by exogenous electrical stimulus and soluble factors." Brain Res. Jan. 1, 2018;1678:288-296. doi: 10.1016/j.brainres.2017.10.032. Epub Oct. 31, 2017. PMID: 29097106.

(56) References Cited

OTHER PUBLICATIONS

The et al. "Mechanistic Roles of Matrilin-2 and Klotho in Modulating the Inflammatory Activity of Human Aortic Valve Cells" Cells 2020, 9, 385; doi:10.3390/cells9020385.

Thurston et al. "Tumor necrosis factor and interferon-gamma downregulate Klotho in mice with colitis". Gastroenterology. Apr. 2010;138(4):1384-94, 1394.e1-2. doi: 10.1053/j.gastro.2009.12.002. Epub Dec. 11, 2009. PMID: 20004202; PMCID: PMC3454518.

Torbus-Paluszczak et al. "Klotho protein in neurodegenerative disorders," Neurol. Sci. 39, 1677-1682 (2018): doi.org/10.1007/s10072-018-3496-x.

Van Kampen et al. "Treatment of Erectile Dysfunction by Perineal Exercise, Electromyographic Biofeedback, and Electrical Stimulation," Phys. Ther. 2003; 83(6):536-543.

Vervloet et al. "Fibroblast growth factor-23 and Klotho in chronic kidney disease" Kidney International Supplements vol. 1, Issue 4, P130-135, Sep. 1, 2011;DOI: https://doi.org/10.1038/kisup.2011.29.

Wang et al. "Correlation between Soluble a-Klotho and Renal Function in Patients with Chronic Kidney Disease: A Review and Meta-Analysis", BioMed Research International, vol. 2018, Article ID 9481475, 12 pages, (Aug. 2018). https://doi.org/10.1155/2018/9481475.

Wang, et al. "Secreted klotho from exosomes alleviates inflammation and apoptosis in acute pancreatitis." American Journal Of Translational Research vol. 11,6 3375-3383. Jun. 15, 2019.

Yamaguchi, "RANK/RANKL/OPG during orthodontic tooth movement", Orthod Craniofac Res. May 2009; 12(2): 113-9. doi: 10.1111/j.1601-6343.2009.01444.x.

Yamakazi et al., "Hair cycle-dependent expression of hepatocyte growth factor (HGF) activator, other proteinases, and proteinase inhibitors correlates with the expression of HGF in rat hair follicles", J Investig Dermatol Symp Proc., 4(3):312-5 (Dec. 1999).

Yang "Effect RANKL Produced by Periodontal Ligament Cells on Orthodontic Tooth Movement" (2016) Dental Theses. Paper 13.

Yang et al. "Effect of Amniotic Fluid Stem Cells and Amniotic Fluid Cells on the Wound Healing Process in a White Rat Model" APS, vol. 40, No. 5 (Sep. 2013).

Yang et al., "Acupuncture for hypertension," Cochrane Database of Systematic Reviews, Available Online at <https://www.cochranelibrary.com/cdsr/doi/10.1002/14651858.CD008821.pub2/full>, (2018), 4 pages.

Yang Lei, "Mechanisms and Reversal of Elastin Specific Medial Arterial Calcification" (2014). All Dissertations, Papei 1307, (available at https://tigerprints.clemson.edu/all_dissertations/1307), 214 pages.

Yarbrough et al., "Specific Binding and Mineralization of Calcified Surfaces by Small Peptides," Calcified Tissue International, vol. 86, (2010), pp. 58-66.

Yildirimer et al. "Skin regeneration scaffolds: a multimodal bottom-up approach" Trends in Biotechnology, Dec. 2012, vol. 30, No. 12, pp. 638-648.

Yoon et al. "Skin Regeneration Effect and Chemical Composition of Essential Oil from Artemisia montana" Natural Product Communications (Sep. 2014) vol. 9, No. 11, pp. 1619-1622.

Yu et al. "Association between inflammation and systolic blood pressure in RA compared to patients without RA" Arthritis Research & Therapy vol. 20, Article No. 107 (2018).

Yu et al. "Effects and mechanisms of a microcurrent dressing on skin wound healing: a review" Military Medical Research (Nov. 2014) 1:24 http://www.mmrjournal.org/content/1/1/24.

Yuan et al. "Electrical stimulation enhances cell migration and integrative repair in the meniscus" Sci Rep 4, 3674 (2014). https://doi.org/10.1038/srep03674.

Zalavras, Charalampos G. "CORR Insights(Registered): Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), pp. 1676-1678.

Zaniboni et al. "Do electrical current and laser therapies improve bone remodeling during an orthodontic treatment with corticotomy?" Clin Oral Invest 23, 4083-4097 (2019). https://doi.org/10.1007/s00784-019-02845-9.

Zaske "Discovery enables adult skin to regenerate like a newborn's" Medical Research, accessed Aug. 4, 2021 https://medicalxpress-com.cdn.ampproject.org/c/s/medicalxpress.com/news/2020-09-discovery-enables-adult-skin-regenerate.amp.

Zdzisinska et al. "RANK/RANKL i OPG w szpiczaku plazmocytowym [The role of RANK/RANKL and OPG in multiple myeloma]" Postepy Hig Med Dosw (Online). 2006; 60:471-482 (Abstract Only).

Zhang et al. "Exosomes derived from human embryonic mesenchymal stem cells promote osteochondral regeneration", Osteoarthritis and Cartilage, vol. 24, Issue 12, Dec. 2016, pp. 2135-2140.

Zhang et al. "Therapeutic potential of stem cells in skin repair and regeneration" Chinese Journal of Traumatology (Apr. 2008) 11(4):209-221.

Zhang et al., "Comparison of arterial stiffness in non-hypertensive and hypertensive population of various age groups," Jan. 24, 2018, 2 pages (Abstract Only).

Zhang et al., "Highly Stable and Reusable Imprinted Ailificial Antibody Used for in Situ Detection and Disinfection of Pathogens," Chemical Science, vol. 6, (2015), pp. 2822-2826.

Zhao et al. "Local osteoprotegerin gene transfer inhibits relapse of orthodontic tooth movement." Am J Orthod Dentofacial Orthop. Jan. 2012; 141(1):30-40. doi: 10.1016/j.ajodo.2011.06.035.

Zhong et al. "TKI-31 inhibits angiogenesis by combined suppression signaling pathway of VEGFR2 and PDGFRbeta" Cancer Biology & Therapy 5:3, 323-330, Mar. 2006.

Zhou et al. "Klotho Ameliorates Kidney Injury and Fibrosis and Normalizes Blood Pressure by Targeting the Renin-Angiotensin System" The American Journal of Pathology, vol. 185, No. 12, Dec. 2015.

Zhou et al. "Klotho Gene Deficiency Causes Salt-Sensitive Hypertension via Monocyte Chemotactic Protein-1/CC Chemokine Receptor 2-Mediated inflammation" J Am Soc Nephrol 26: 121-132, 2015 (Accepted Apr. 2014).

Zimmerman et al. "Cancer cell proliferation is inhibited by specific modulation frequencies" Br J Cancer. Jan. 17, 2012;106(2):307-13. doi: 10.1038/bjc.2011.523. Epub Dec. 1, 2011. PMID: 22134506; PMCID: PMC3261663.

Zimmerman et al. "Targeted treatment of cancer with radiofrequency electromagnetic fields amplitude-modulated at tumor-specific frequencies" Chin J Cancer. Nov. 2013;32(11):573-81. doi: 10.5732/cjc.013.10177. PMID: 24206915; PMCID: PMC3845545.

Zupan et al. "The relationship between osteoclastogenic and anti-osteoclastogenic pro-inflammatory cytokines differs in human osteoporotic and osteoarthritic bone tissues," Journal of Biomedical Science, 2012, 19:28 (DOI: 10.1186/1423-0127-19-28).

"Electric Tumor Treatment Fields," No. 0827 Policy, aetna.com/cpb/medical/data/800_899/0827.html (Nov. 18, 2016), last visited Sep. 12, 2018.

"Electrical brain stimulation could support stroke recovery," sciencedaily.com/releases/2016/03/160316151108.htm (Mar. 16, 2016), last visited Sep. 12, 2018.

"FDA Approves Algovita Spinal Cord Stimulation System from Greatbatch," http://www.odtmag.com/contents/view_breaking-news/2015-12-02/fda-approves-algovita-spinal-cord-stimulation-jystem-from-greatbatch (Dec. 2, 2015).

Abdel-Rehim "Change of serum klotho protein and its relationship with endothelial dysfunction, oxidative stress and arterial aging in essential hypertensive patients" J Kidney 2018, vol. 4 (Dec. 2018).

Abdel-Rehim "Change of serum klotho protETn and its relationship with endothelial dysfunction, oxidative stress and arterial aging in essential hypertensive patients" J Kidney 2018, vol. 4 (Dec. 2018).

Ahrens et al. "Klotho expression is a prerequisite for proper muscle stem cell function and regeneration of skeletal muscle" Ahrens et al. Skeletal Muscle (Jul. 2018) 8:20 pp. 1-14.

Akbari et al. "Association of Klotho gene polymorphism with hypertension and coronary artery disease in an Iranian population" BMC Cardiovascular Disorders (Dec. 2018) 18:237.

(56) References Cited

OTHER PUBLICATIONS

Alghatrif et al. "The Conundrum of Arterial Stiffness, Elevated blood pressure, and Aging" Curr Hypertens Rep. Feb. 2015; 17(2): 12. doi: 10.1007/s11906-014-0523-z.

Almpani et al., "Nonsurgical Methods for the Acceleration of the Orthodontic Tooth Movement", Tooth Movement. Fronl Oral Biol., vol. 18, pp. 80-91 (Karger, Basel, CH 2016) (DOI: 10.1159/000382048), Published online: Nov. 24, 2015.

Andersson et al. "Drinking, antidiuresis and milk ejection from electrical stimulation within the hypothalamus of the goat," Acta Physiol Scand. Dec. 31, 1955; 35(2):191-201; DOI: 10.1111/j.1748-1716.1955.tb01277.x.

Ando et al."RANKL/RANK/OPG: key therapeutic target in bone oncology" Curr Drug Discov Technol. Sep. 2008; 5(3): 263-268.

Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/105873.

Aronowitz et al. "Mechanical versus enzymatic isolation of stromal vascular fraction cells from adipose tissue" SpringerPlus (2015) 4:713 DOI 10.1186/s40064-015-1509-2.

ASPS, "Stem Cell Treatments 'Go Deep' to RegenerateSun-Damaged Skin" Article, American Society of Plastic Surgeons (May 27, 2020) 4 pages.

Atkinson et al. "Bioelectric Properties of the Tooth" 1969 vol. 48 issue: 5, pp. 789-794.

Aubert et al. "A new ultrasonic process for a renewal of aortic valve decalcification" Cardiovascular Ultrasound 2006, 4:2 doi:10.1186/1476-7120-4-2.

Aydin et al., "Focusing of Electromagnetic Waves by a Left-Flanded Metamaterial Flat Lens," vol. 13, (2005), pp. 8753-8759.

Back et al. "Endogenous Calcification Inhibitors in the Prevention of Vascular Calcification: A Consensus Statement From the COST Action EuroSoftCalcNet" Frontiers in Cardiovascular Medicine | www.frontiersin.org, Jan. 2019 | vol. 5 | Article 196.

Banerjee et al. "MicroRNAs in Skin and Wound Healing" Methods Mol Biol. 2013; 936: 343-356, Author manuscript (Mar. 2015).

Banerjee, P. "Electrical muscle stimulation for chronic heart failure: an alternative tool for exercise training?" Curr Heart Fail Rep., 7(2):52-8. doi: 10.1007/s11897-010-0013-9 (Jun. 2010).

Bang et al., "Attenuation of Hypertension by C-Fiber Stimulation of the Human Median Nerve and the Concept-Based Novel Device," Scientific Reports, vol. 8, (2018), 12 pages.

Barbault et al., Amplitude-modulated electromagnetic fields for the treatment of cancer: Discovery of tumor-specific frequencies and assessment of a novel therapeutic approach, Journal of Experimental & Clinical Cancer Research, Apr. 14, 2009, vol. 28, No. 51, doi:10.1186/1756-9966-28-51, 10 pages.

Barker et al., "A Formidable Foe is Sabotaging Your Results: What You Should Know About Biofilms and Wound Flealing," Plastic and Reconstructive Surgery, vol. 139, (2017), pp. 1184e-1194e.

Barnhill "It's Electric! All About Microcurrent Facials" accessed Aug. 4, 2021, https://intothegloss.com/2016/04/microcurrent-treatment/.

Basu et al. "Exosomes for repair, regeneration and rejuvenation" Expert Opinion on Biological Therapy, 16:4, 489-506, DOI: 10.1517/14712598.2016.1131976.

Beebe et al. "Bioelectric Applications for Treatment of Melanoma," Cancers (Basel). Sep. 2010; 2(3): 1731-1770, published online Sep. 27, 2010; doi: 10.3390/cancers20317.

Beitelshees b1 AL. "CXCL5 polymorphisms are associated with variable blood pressure in cardiovascular disease-free adults" Hum Genomics. 2012; 6(1): 9.

Berman "Suzanne Somers' Experimental Breast Reconstruction" Medpage Today, Feb. 7, 2012, www.medpagetoday.com > blogs > celebritydiagnosis.

Beugels et al. "Electrical stimulation promotes the angiogenic potential of adipose-derived stem cells" Scientific Reports (Aug. 2019) 9:12076.

Bi et al. "Key Triggers of Osteoclast-Related Diseases and Available Strategies for Targeted Therapies: A Review" Front Med (Lausanne). 2017; 4: 234. doi: 0.3389/fmed.2017.00234.

Bioleohardnew, "Leonhardt Ventures Files Patent for Heart Valve Regeneration," (available at https://bioleonhardt.com/leonhardt-ventures-files-patent-for-heart-valve-regeneration/), (Mar. 20, 2018), 6 pages.

Blood Vessels Hold Key To Thicker Hair Growth, https://www.sciencedaily.com/releases/2001/02/010215074636.htm (Feb. 2001).

Blum "Role of cytokines in heart failure," American Heart Journal, vol. 135, Issue 2, Feb. 1998, pp. 181-186; doi.org/10.1016/S0002-8703(98)70080-8.

Borden et al., "Electric Current-Induced Detachment of *Staphylococcus epidermidis* Biofilms from Surgical Stainless Steel," Applied and Environmental Microbiology, vol. 70, (2004), pp. 6871-6874.

Borgobello, B. "FDA approves the treatment of brain tumors with electrical fields," New Atlas, http://newatlas.com/treatment-of-brain-tumors-with-electrical-fields/21433/(Feb. 13, 2012), last visited Sep. 12, 2018.

Botchkareva "MicroRNA/mRNA regulatory networks in the control of skin development and regeneration" Cell Cycle 11:3, 468-474; (Feb. 2012) Landes Bioscience.

Boyle "Wound-Treating Jelly Regenerates Fresh, Scar-Free Skin", Popular Science, (Dec. 15, 2011), "New material developed for accelerated skin regeneration in major wounds", Science Highlight, (National Institute of Biomedical 11 Imaging and Bioengineering, Dec. 17, 2015).

Bradshaw et al. "Designer self-assembling hydrogel scaffolds can impact skin cell proliferation and migration" Nature Scientific Reports, vol. 4, Article No. 6903 (2014).

Brooks et al. "Bioelectric impedance predicts total body water, blood pressure, and heart rate during hemodialysis in children and adolescents" J. Ren Nutr., 18(3):304-311 (May 2008); doi: 10.1053/j.jm.2007.11.008.

Buckle et al. "Soluble Rank Ligand Produced by Myeloma Cells Causes Generalised Bone Loss in Multiple Myeloma" PLoS One. 2012; 7(8): e41127. doi: 10.1371/journal.pone.0041127 PMCID: PMC3430669.

Cai et al., "Intermedin Inhibits Vascular Calcification by Increasing the Level of Matrix (Gamma)-Carboxyglutamic Acid Protein," Cardiovascular Research, vol. 85, (2010), pp. 864-873.

CalXStars Business Accelerator, Inc.—Website—Justia Patents—Mar. 15, 2017—US Patent Application for Stimulator, Pump & Composition Patent Application (Application #20170266371) https://protect-us.mimecast.com/s/tSaBCxkVlwuDr61CvMWbF?domain=patents.justia.com.

Campbell et al. "Electrical stimulation to optimize cardioprotective exosomes from cardiac stem cells" Med Hypotheses. Mar. 2016; 88:6-9. doi: 10.1016/j.mehy.2015.12.022. Epub Jan. 11, 2016.

Canty et al., "Antibiotics Enhance Prevention and Eradication Efficacy of Cathodic-Voltage-Controlled Electrical Stimulation against Titanium-Associated Melhicillin-Resistant *Staphylococcus aureus* and Pseudomonas aeruginosa Biofilms," mSphere, vol. 4, (May/Jun. 2019), e00178-19, 14 pages.

Carboni et al. "An initial study on the effect of functional electrical stimulation in erectile dysfunction: a randomized controlled trial" IJIR: Your Sexual Medicine Journal (May 2018) 30:97-101.

Caubet et al., "A Radio Frequency Electric Current Enhances Antibiotic Efficacy Against Bacterial Biofilms," Antimicrobial Agents and Chemotherapy, vol. 48, (2004), vol. 4662-4664.

Cerrada et al., "Hypoxia-Inducible Factor 1 Alpha Contributes to Cardiac Healing in Mesenchymal Stem Cells-Mediated Cardiac Repair," Stem Cells and Development, 22(3): 501-511 (2013).

Cervera "The interplay between genetic and bioelectrical signaling permits a spatial regionalisation of membrane potentials in model multicellular ensembles," Nature, Scientific Reports, Oct. 12, 2016 vol. 6, Article No. 35201 (2016).

Chaikin et al. "Microcurrent stimulation in the treatment of dry and wet macular degeneration" Clinical Ophthalmology 2015:9 2345-2353 (Dec. 2015).

(56) References Cited

OTHER PUBLICATIONS

Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Somayaji et al., "In Vitro Scanning Electron Microscopic Study on the Effect of Doxycycline and Vancomycin on Enterococcal Induced Biofilm," Iranian Endodontic Journal, vol. 5, (2010), pp. 53-58.
Souli et al., "Effects of Slime Produced by Clinical Isolates of Coagulase-Negative Staphylococci on Activities of Various Antimicrobial Agents," Antimicrobial Agents and Chemotherapy, vol. 42, (Apr. 1998), pp. 939-941.
Spadari et al., Electrical stimulation enhances tissue reorganization during orthodontic tooth movement in rats; Clinical Oral Investigations, Jan. 2017, vol. 21, Issue 1, pp. 111-120, Abstract.
Spiridonov et al. "Effect of Transcutaneous Electrical Stimulation of Nerves on Blood Pressure and Blood Content of Neuropeptide CGRP and Nitric Oxide in Hypertensive Rats with Metabolic Disturbances" Bull Exp Biol Med (Feb. 2019) 166: 436-437.
Stein et al., "The effect of transcutaneous electrical nerve stimulation on blood pressure," Blood Pressure, vol. 22, Issue 3, 2013, available online at < https://www.tandfonline.com/doi/full/10.3109/08037051.2012.722271 >, 5 pages.
Stenn et al., "Bioengineering the Hair Follicle," Organogenesis, 3(1): 6-13 (Jan.-Mar. 2007).
Stewart b I al., "Electrolytic Generation of Oxygen Partially Explains Electrical Enhancement of Tobramycin Efficacy Against Pseudomonas Aeruginosa Biofilm," Antimicrobial Agents and Chemotherapy, vol. 43, (1999), pp. 292-296.
Stoodley b I al., "Influence of Electric Fields and pH on Biofilm Structure as Related to the Bioelectric Effect," Antimicrobial Agents and Chemotherapy, vol. 41, (1997), pp. 1876-1879.
Su et al. "Klotho protein lowered in elderly hypertension" Int J Clin Exp Med (Aug. 2014) 7(8):2347-2350.
Sultana et al., "Electrochemical Biofilm Control: A Review," Biofouling, vol. 31, (2015), pp. 745-758.
Sun "Regulation of Blood Pressure by Klotho" University of Oklahoma Health Sciences Center, Oklahoma City, OK, United States; accessed Jun. 2, 2021; https://grantome.com/grant/NIH/R01-HL102074-01A1.
Sun et al. "Amniotic fluid stem cells provide considerable advantages in epidermal regeneration: B7H4 creates a moderate inflammation microenvironment to promote wound repair" Scientific Reports (Jun. 2015) 5:11560, DOI: 10.1038/srep11560.
Sutherland et al. "Prolonged electrical stimulation of the nipples evokes intermittent milk ejection in the anaesthetised lactating rat," Exp Brain Res. 1987;66(1):29-34.
Szkotak et al., "Differential Gene Expression to Investigate the Effects of Low-Level Electrochemical Currents on Bacillus subtilis," AMB Express, vol. 1, (Nov. 2011), 12 pages.
Tajima et al. "HIF-1alpha is necessary to support gluconeogenesis during liver regeneration" Biochem Biophys Res Commun. Oct. 2, 2009; 387(4):789-94. doi: 10.1016/j.bbrc.2009.07.115. Epub Jul. 28, 2009.
Takenaka et al. "Klotho Supplementation Attenuatesblood Pressure and Cyst Growth Inmouse Polycystic Kidney Disease" Journal of Hypertension: vol. 36—Issue—p. e76 (Jun. 2018).
Tamaki et al. "Cardiomyocyte Formation by Skeletal Muscle-Derived Multi-Myogenic Stem Cells after Transplantation into Infarcted Myocardium," PLoS One 3(3): e1789. doi:10.1371/journal.pone.0001789 (Mar. 2008).
Tan et al. "Bioelectric Perturbations in Orthodontic tooth movement" 2010 Journal of Dental Sciences & Research 1:1: pp. 41-49.
Tan et al., "Acupuncture Therapy for Essential Hypertension: a Network Meta-Analysis," Annals of Translational Medicine, vol. 7, (2019), pp. 1-12.
Tavlasoglu et al. "Is partial decalcification of posterior mitral annular bed logical in all mitral valve replacement procedures?" European Journal of Cardio-Thoracic Surgery 43 (2013) 449-450.

Thattaliyath et al. "Modified Skeletal Myoblast Therapy For Cardiac Failure Using AAV SDF-1," Proc. Inti. Soc. Mag. Reson. Med. 16, p. 579 (2008).
Tokyo Medical and Dental University "RANKL expressed by osteocytes has an important role in orthodontic tooth movement" Science Daily Oct. 20, 2017.
Totsugawa, et al. "Ultrasonic annular debridement in minimally invasive aortic valve replacement" Gen Thorac Cardiovasc Surg. Jan. 2020;68(1):81-83. doi: 10.1007/s11748-019-01158-8. Epub Jun. 15, 2019. (Abstract Only).
Trafton, Anne, "A Noninvasive Method for Deep Brain Stimulation," MIT News Office, (available at http://news.mil.edu/2017/noninvasive-method-deep-brain-stimulation-0601), (Jun. 1, 2017), 3 pages.
Tsang et al. "Large animal models of cardiovascular disease" Cell Biochemistry and Function (Feb. 2016) vol. 34, Issue 3 p. 113-132.
Tyler "Nature's Electric Potential: A Systematic Review of the Role of Bioelectricity in Wound Healing and Regenerative Processes in Animals, Humans, and Plants" Front. Physiol., (Sep. 2017) https://doi.org/10.3389/fphys.2017.00627.
UCIrvine, "Electroacupuncture for Hypertension in Women: The Susan Samueli Center for Integrative Medicine at UC Irvine is Recruiting Patients for a Study", Principle Investigators: Dr. Stephanie Tjen-a-Looi and Dr. Shaista Malik, MOD# 20266, HS# 1999-2222, (2017), 1 page.
Ueland et al. "Inflammatory cytokines as biomarkers in heart failure," Clinica Chimica Acta, vol. 443, Mar. 30, 2015, pp. 71-77; doi.org/10.1016/j.cca.2014.09.001.
Valvublator Heart Valve Regeneration, accessed Apr. 24, 2020 https://valvublator.com (6 pages).
Van Dam et al. "RANK/RANKL signaling inhibition may improve the effectiveness of checkpoint blockade in cancer treatment" Critical Reviews in Oncology/Hematology vol. 133, Jan. 2019, pp. 85-91.
Verna et al. "The rate and the type of orthodontic tooth movement is influenced by bone turnover in a rat model" European Journal of Orthodontics 22 (2000) 343-352.
Vig et al. "Advances in Skin Regeneration Using Tissue Engineering" Int. J. Mol. Sci. (Apr. 2017), 18, 789; doi:10.3390/ijms18040789.
Vilela-Martin et al., "Effects of Transcutaneous Electrical Nerve Stimulation (TENS) on Arterial Stiffness and Blood Pressure in Resistant Hypertensive Individuals: Study Protocol for a Randomized Controlled Trial," Trials, vol. 17, (2016), pp. 1-13.
Villemain et al. Pulsed Cavitational Ultrasound Softening : A New Noninvasive Therapeutic Approach for Calcified Bioprosthetic Valve Stenosis' JACC: Basic to Translational Science vol. 2, Issue 4, Aug. 2017, pp. 372-383.
Wagenseil et al., "Elastin in large artery stiffness and hypertension," Journal of Cardiovascular Translational Research, vol. 5, No. 3, 2012, pp. 264-273, Available online at < https://www.ncbi.nlm.nih.gov/pmc/articles/PMC3383658/ >, 21, pages.
Walsh & Choi "Biology of the RANK* RAN* OPG System in Immunity, Bone, and Beyond", Front Immunol. 2014; 5:511.
Wang el al., "Controlling *Streptococcus mutans* and *Staphylococcus aureus* Biofilms With Direct Current and Chlorhexidine," AMB Express, vol. 7, (Nov. 2017), 9 pages.
Wang et al. "Local and sustained miRNA delivery from an injectable hydrogel promotes cardiomyocyte proliferation and functional regeneration after ischemic injury", Nat Biomed Eng. 2017; 1: 983-992, doi: 10.1038/S41551-017-0157-y.
Warner "Inflammation Adds to Blood Pressure Risks, High Blood Pressure and C-Reactive Protein May Trigger Heart Attack, Stroke" Art. WebMD Health News (2003) 2 pages.
Wei et al. "Nanofat-derived stem cells with platelet-rich fibrin improve facial contour remodeling and skin rejuvenation after autologous structural fat transplantation" Research Paper, Oncotarget (Jul. 2017) vol. 8, (No. 40), pp. 68542-68556.
Wei et al., "Epicardial FSTL1 reconstitution regenerates the adult mammalian heart," Nature 525: 479-485 (Sep. 24, 2015).
Welch "RGS2 Proteins Regulate Blood Pressure" JASN Nov. 2010, 21 (11) 1809-1810.

(56) References Cited

OTHER PUBLICATIONS

Wellman et al., "Bacterial Biofilms and the Bioelectric Effect," Antimicrobial Agents and Chemotherapy, vol. 40, (1996), pp. 2012-2014.

Westermark et al. "Effect of externally applied focused acoustic energy on clot disruption in vitro" Clinical Science 97(1):67-71 (Jul. 1999); DOI:10.1042/CS19980379.

What Is Elastin? http://www.keracyte.com/index.php/site/page?view=whatIsElastin.

Wong el al., "Dual Functional Polyelectrolyte Multilayer Coatings for Implants: Permanent Microbicidal Base With Controlled Release of Therapeutic Agents," Journal of the American Chemical Society, vol. 132, (2010), pp. 17840-17848.

Wu et al. "MSC-exosome: A novel cell-free therapy for cutaneous regeneration" Cytotherapy, vol. 20, Issue 3, (Mar. 2018) pp. 291-301, https://www.sciencedirect.com/science/article/pii/S146532491730717X.

Wu et al. "Validation study toward measuring the mechanical properties of blood clots using resonant acoustic spectroscopy with optical vibrometry." Proceedings of SPIE—the International Society for Optical Engineering vol. 8214 (epub Feb. 2012): 82140G. doi:10.1117/12.906956.

Wu et al., "Vascular Calcification: an Update on Mechanisms and Challenges in Treatment," Calcified Tissue International, vol. 93, (Oct. 2013), pp. 365-373.

Xiong el al. "Current understanding of neuroinflammation after traumatic brain injury and cell-based therapeutic opportunities" Chin J Traumatol. Jun. 2018; 21(3): 137-151. doi: 10.1016/j.cjtee.2018.02.003.

Jamal et al. "Klotho, Hypertension and Arterial Stiffness: A Review" Austin J Nephrol Hypertens.(Jul. 2019) 6(2):1082.

Jansen et al. "Stimulation of osteogenic differentiation in human osteoprogenitor cells by pulsed electromagnetic fields: an in vitro study" BMC Musculoskelelal Disorders (2010) 11:188 DOI: 10.1186/1471-2474-11-188.

JCCR "Emerging roles of klotho in cardiovascular diseases%5D" Accessed Jun. 2, 2021 https://medcraveonline.com/JCCR/emerging-roles-of-klotho-in-cardiovascular-diseases.html%5D.

Jeffrey, "How to Decalcify Your Pineal Gland (And Why It's Really Important for Higher Mental Performance)," (available at https://scottjeffrey.com/decalcify-your-pineal-gland/). Retrieved on May 23, 2019, 23 pages.

Jia at al., "Activin B Promotes Initiation and Development of Hair Follicles in Mice" Cells Tissues Organs, 198:318-326 (Feb. 2014).

Jing-Hong et al. "Electrochemical Therapy of Tumors" Hindawi Publishing Corporation, Conference Papers in Medicine, vol. 2013, Article ID 858319, 13 pages, http://dx.doi.org/10.1155/2013/858319.

John el al. "Growth Factors in Skin Care—Series Introduction" (Mar. 2015) website accessed Aug. 4, 2021 http://barefacedtruth.com/2015/03/28/growth-factors-skin-care-introduction/.

Jouybar et al. "Enhanced Skin Regeneration by Herbal Extract-Coaled Poly-L-Lactic Acid Nanofibrous Scaffold" Artif Organs. Nov. 2017; 41(11):E296-E307. doi: 10.1111/aor.12926 (Abstract Only).

Jung et al. "Prospective 1-Year Follow-Up Study of Breast Augmentation by Cell-Assisted Lipotransfer" Aesthetic Surgery Journal 2016, vol. 36(2) 179-190 © 2015 The American Society for Aesthetic Plastic Surgery, Inc.

Kanno et al., Establishment of a Simple and Practical Procedure Applicable to Therapeutic Angiogenesis, Circulation, 1999, pp. 2682-2687, vol. 99.

Kanzaki et al. "Local OPG gene transfer to periodontal tissue inhibits orthodontic tooth movement." J Dent Res 2004; 83:92/ 925.

Kanzaki et al. "Local RANKL gene transfer to the periodontal tissue accelerates orthodontic tooth movement", Gene Therapy, (2006) 13, 678-685.

Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002; 17:21 / 220.

Kasimanickam et al., "Prevention and Treatment of Biofilms by Hybrid- and Nanotechnologies," International journal of Nanomedicine, vol. 8, (2013), pp. 2809-2819.

Kaur et al. "Electrically conductive polymers and composites for biomedical applications", RSC Adv., 2015, 5, 37553-37567 DOI: 10.1039/C5RA01851J.

Kawagishi et al. S"onic hedgehog signaling regulates the mammalian cardiac regenerative response" Journal of Molecular and Cellular Cardiology; vol. 123, P180-184 (Oct. 2018).

Keles et al. "Inhibition of tooth movement by osteoprotegerin vs. pamidronate under conditions of constant orthodontic force", Eur J Oral Sci. Apr. 2007; 115(2):131-6.

Keunen et al. "Anti-VEGF treatment reduces blood supply and increases tumor cell invasion in glioblastoma," Proc. Natl. Acad. Sci. U.S. A. Mar. 1, 2011; 108(9):3749-3754, published online Feb. 14, 2011; doi: 10.1073/pnas.1014480108.

Khan et al. "Accelerating Tooth Movement What Options We Have?" J Dent Health Oral Disord Ther 2016, 5(7):00181.

Kido et al. "Hypoxia-Inducible Factor 1-Alpha Reduces Infarction and Attenuates Progression of Cardiac Dysfunction After Myocardial Infarction in the Mouse" JACC, vol. 46, Issue 11, Dec. 6, 2005, pp. 2116-2124. https://doi.org/10.1016/j.jacc.2005.08.045.

Kim et al. "Hyaluronate—Epidermal Growth Factor Conjugate for Skin WoundHealing and Regeneration" Biomacromolecules (Oct. 2016) 17 , 11, 3694-3705 (Abstract Only) Publication Date : Oct. 24, 2016.

Kim et al. "Picking Winners and Losers: Cell Competition in Tissue Development and Homeostasis" vol. 36, Issue 7, p. 490-498, Jul. 1, 2020 (Abstract Only).

Kim et al., "Effect of Electrical Energy on the Efficacy of Biofilm Treatment Using the Bioelectric Effect," NPJ Biofilms and Microbiomes, vol. 1, (2015), Article 15016, 8 pages.

Kim et al., The effects of electrical current from a micro-electrical device on tooth movement, Korean Drthod., Oct. 2008, 38(5):337-346, Abstract submitted in English.

King et al. "Mechanical Decalcification of the Aortic Valve" 272 The Annals of Thoracic Surgery vol. 42 No. 3 Sep. 1986 (pp. 269-272).

Kinney et al., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine, vol. 51, (2019), pp. 40-46.

Kondo et al. "Types of tooth movement, bodily or tipping, do not affect the displacement of the tooth's center of resistance but do affect the alveolar bone resorption" Angle Orthod Jul. 2017; 87(4):563-569.

Kose et al. "Citric acid as a decalcifying agent for the excised calcified human heart valves" Anadolu Kardiyol Derg 2008; 8: 94-8 (Eng Abstract).

Krishnan et al. (eds.), "Biological Mechanisms of Tooth Movement", John Wiley & Sons 2015 (10 pages).

Lam et al. "Mesenchymal stem cell therapies for skin repair and regeneration" J Dermat Cosmetol. (Aug. 2017) vol. 1, Issue 3, pp. 62?64.

Lamoureux et al. "Therapeutic Relevance of Osteoprotegerin Gene Therapy in Osteosarcoma: Blockade of the Vicious Cycle between Tumor Cell Proliferation and Bone Resorption" Cancer Res 1 2007 67(15):7308-7318; DOI: 10.1158/0008-5472.CAN-06-4130.

Landau et al. "Review: Proposed Methods to Improve the Survival of Adipose Tissue in Autologous Fat Grafting" Plast Reconstr Surg Glob Open. 2018;6(8):e1870. Published Aug. 3, 2018. doi:10.1097/GOX.0000000000001870.

Lanzetto et al. "Fundamental principles of an anti-VEGF treatment regimem optimal application of intravitreal anti-vascular endothelial growth factor therapy of macular diseases," Graefes Arch. Clin. Exp. Ophthalmol. 2017; 255(7)11259-1273 (published online May 19, 2017); doii 10.1007/s00417-017-3647-4.

(56) References Cited

OTHER PUBLICATIONS

Lasserre et al., "Influence of Low Direct Electric Currents and Chlorhexidine Upon Human Dental Biofilms," Clinical and Experimental Dental Research, vol. 2, (Jul. 2016), pp. 146-154.
Lasserre et al., "Oral Microbes, Biofilms and Their Role in Periodontal and Peri-Implant Diseases," Materials, vol. 11, (Sep. 2018), Article 1802, 17 pages.
Ledzewicz et al. "Analysis of optimal controls for a mathematical model of tumor anti-angiogenesis" Optim. Control Appl. Meth. 2006; 00:1-16.
Lee et al. "Hepatocyte growth factor (HGF) activator expressed in hair follicles is involved in in vitro HGF-dependent hair follicle elongation," J. Dermatol. Sci., 25(2): 156-63 (Feb. 2001).
Lee et al., "Targeted Release of Tobramycin From a pH-Responsive Grafted Bilayer Challenged With *S. aureus*," Biomacromolecules, vol. 16, (2015), pp. 650-659.
Lei et al., "Efficacy of Reversal of Aortic Calcification by Chelating Agents," Calcified Tissue International, vol. 93, (Nov. 2013), 15 pages.
Leibrock et al., "NH4CI Treatment Prevents Tissue Calcification in Klotho Deficiency," Journal of the American Society of Nephrology, vol. 26, (2015), pp. 2423-2433.
Leonhardt "Micro Stimulator" http://www.bioleonhardt.com/microstimulator/.
Leonhardt "Leonhardt Adds HIF-1 Alpha To Estate of Bioelectric Controlled Release Regenerative Proteins" Press Release, Published Jun. 13, 2017.
Leonhardt "PressureStim Blood Pressure Control" accessed Jun. 2, 2021, https://pressurestim.com.
Leonhardt "PressureStim Receives IRB Approval to Launch Bioelectric Hypertension Treatment Clinical Study" Accessed Jun. 2, 2021, https://www.prdistribution.com/news/pressurestim-receives-irb-approval-to-launch-bioelectric-hypertension-treatment-clinical-study-2.html?fbclid=IwAR28Dh97RAKXXHrfgUONKW1pk-MWyeF_ibUIpQc_2XEN32C6sS%E2%80%A6.
Leonhardt, H.—Leonhardt Announces Vibrational Energy Device For Preventing Blood Clots Provisional Patent Application and License Agreements, (available at https://leonhardtventures.com/leonhardt-announces-vibrational-energy-device-preventing-blood-clots-provisional-patent-application-license-agreements/), (July 5, 2017), 5 pages.
Leonhardt's Launchpads Announces Filing of Patent for Bioelectric Stimulation Controlled Klotho Expression—Powerful Anti-aging and Regeneration Promoting Protein, by API Podder, Published: Mar. 13, 2019, available online at < https://mysocialgoodnews.com/leonhardts-launchpads-announces-filing-of-patent-for-bioelectric-stimulation-controlled-klotho-expression-powerful-anti-aging-and-regeneration-promoting-protein/.
Li "Regulation of Renal Oxygenation and Blood Pressure" Art. Virginia Commonwealth University, Richmond, VA, United States (Abstract).
Li et al., "Exogenous IGF-1 promotes hair growth by stimulating cell proliferation and down regulating TGF-(Beta)1 in C57BL/6 mice in vivo" Growth Hormone & IGF Research, vol. 24, Issues 2-3, pp. 89-94 (Apr.-Jun. 2014).
Li et al., "Long-Lasting Reduction of Blood Pressure by Electroacupuncture in Patients with Hypertension: Randomized Controlled Trial," Medical Acupuncture, vol. 27, No. 4, (2015), pp. 253-266.
Li et al., "Repetitive Electroacupuncture Attenuates Cold-Induced Hypertension through Enkephalin in the Rostral Ventral Lateral Medulla," Scientific Reports, vol. 6, (2016), 10 pages.
Brooks et al., "Bioelectric impedance predicts total body water, blood pressure, and heart rate during hemodialysis in children and adolescents" J. Ren Nutr., 18(3):304-311 (May 2008); doi: 10.1053/j.jrn.2007.11.008.
Bruggemann et al. "Effects of Neuromuscular Electrical Stimulation During Hemodialysis on Peripheral Muscle Strength and Exercise Capacity: A Randomized Clinical Trial." Arch Phys Med Rehabil. May 2017;98(5):822-831.e1. doi: 10.1016/j.apmr.2016.12.009. Epub Jan. 16, 2017. (Abstract Only).
Chen et al. "Secreted Klotho Attenuates Inflammation-Associated Aortic Valve Fibrosis in Senescence-Accelerated Mice P1" Hypertension May 2018; 71:877-885.
Chernet "Transmembrane voltage potential is an essential cellular parameter for the detection and control of tumor development in a Xenopus model," Dis. Models & Mech. 6, pp. 595-607 (2013); doi:10.1242/dmm.010835.
Columbia "Implant Procedure Concepts—Pacemaker, ICD and CRT Overview," columbia.edu/itc/hs/medical/hickey/docs/Pacemaker,%20ICD%20and%20CRT%20Overview%20022007.pdf.
Dalise et al., "Biological effects of dosing aerobic exercise and neuromuscular electrical stimulation in rats", Sci Rep. Sep. 7, 2017; 7(1):10830.
Dilorio "High-frequency external muscle stimulation in acute kidney injury (AKI): potential shortening of its clinical course" Clinical Nephrology, vol. 78—No. Suppl. Jan. 2012 (S37-S45).
Fatemi et al., "Imaging elastic properties of biological tissues by low-frequency harmonic vibration" Proceedings of the IEEE, 91(10):1503-1519 (Oct. 2003).
Ferrari "The Effect of Electrical Stimulation on Aged Skeletal Muscle Regenerative Potential" http://d-scholarship.pitt.edu/28094/1/FerrariRJ_ETD_May_31_2016_PDF.pdf.
Hopkins Medicine "Overview of Pacemakers and Implantable Cardioverter Defibrillators (ICDs)," hopkinsmedicine.org/healthlibrary/conditions/cardiovascular_diseases/overview_of_pacemakers_and_implantable_cardioverter_defibrillators_icds_85,P00234/.
International Search Report for International Application No. PCT/US2020/021556, dated Jun. 29, 2020, 3 pages.
International Written Opinion for International Application No. PCT/US2020/021556, dated Jun. 29, 2020, 4 pages.
Klotho et al. "Klotho expression in osteocytes regulates bone metabolism and controls bone formation" Kidney International (2017) 92, 599-611.
Prochazka et al., "Cocktail of Factors from Fat-derived Stem Cells Shows Promise for Critical Limb Ischemia" http://www.sciencenewsline.com/news/2016012204520017.html (Jan. 21, 2016).
Ranjit et al., "Potential neuroprotective role of astroglial exosomes against smoking-induced oxidative stress and HIV-1 replication in the central nervous system," Expert Opin Ther Targets. Aug. 2018; 22(8):703-714.
Salcedo et al., "Low current electrical stimulation upregulates cytokine expression in the anal sphincter," Int. J. Colorectal Dis., Feb. 2012;27(2):221-5. doi: 10.1007/s00384-011-1324-3 Epub (Oct. 2011).
Sanchez-Nino et al. "Klotho to Treat Kidney Fibrosis" J Am Soc Nephrol 24: 687-689, 2013. doi: 10.1681/ASN.2013030294.
Schardong et al. "Intradialytic neuromuscular electrical stimulation reduces DNA damage in chronic kidney failure patients: a randomized controlled trial," (Mar. 2018) Biomarkers, 23:5, 495-501, DOI: 10.1080/1354750X.2018.1452049.
Schardong et al. "Effects of Intradialytic Neuromuscular Electrical Stimulation on Strength and Muscle Architecture in Patients With Chronic Kidney Failure: Randomized Clinical Trial." Artif Organs. Nov. 2017;41(11):1049-1058. doi: 10.1111/aor.12886. Epub Jun. 16, 2017. (Abstract Only).
Takenaka et al. "Klotho protein supplementation reduces blood pressure and renal hypertrophy in db/db mice, a model of type 2 diabetes" Acta Physiol (Oxf.) Feb. 2019; 225(2):e13190. doi: 10.1111/apha.13190. Epub Oct. 16, 2018.
Zhu et al. "Klotho controls the brain-immune system interface in the choroid plexus" E11388-E11396 PNAS, vol. 115, No. 48, www.pnas.org/cgi/doi/10.1073/pnas.1808609115 accessed Apr. 12, 2019.
Li et al., "The Mechanism of Acupuncture in Treating Essential Hypertension: A Narrative Review," International Journal of Hypertension, vol. 2019, (2019), Article ID 8676490, 10 pages.
Li, et al. "Local injection of RANKL facilitates tooth movement and alveolar bone remodelling." Oral Diseases, 25(2), 550-560. https://doi.org/10.1111/odi.13013.

(56) References Cited

OTHER PUBLICATIONS

Liang et al. "Therapeutic effect of low-intensity pulsed ultrasound on temporomandibular joint injury induced by chronic sleep deprivation in rats" Am J Transl Res. 2019; 11(6): 3328-3340.

Liesz et al. Editorial: Mechanisms of neuroinflammation and inflammatory neurodegeneration in acute brain injury Front. Cell. Neurosci., 2015. doi://doi.org/10.3389/fncel.2015.00300.

LifeWave X39 (Trademark) Patches; website access Aug. 4, 2021 https://lifewave.com/corporphan/store/product/39000.022.009/.

Lobo-Silva et al. "Balancing the immune response in the brain: IL-10 and its regulation," Journal of Neuroinflammation, 13:297 (2016); doi.org/10.1186/s12974-016-0763-8.

Loizzi et al. "Biological Pathways Involved in Tumor Angiogenesis and Bevacizumab Based Anti-Angiogenic Therapy with Special References to Ovarian Cancer" International Journal of Molecular Sciences. (Sep. 2017); 18(9):1967. https://doi.org/10.3390/ijms18091967.

Longhurst et al. "Evidence-based blood pressure reducing actions of electroacupuncture: mechanisms and clinica application" Sheng Li Xue Bao. Oct. 25, 2017; 69(5): 587-597.

Lop et al., Cutting-Edge Regenerative Medicine Technologies for the Treatment of Heart Valve Calcification, Calcific Aortic Valve Disease, (2013), (available at http://dx.doi.org/10.5772/55327), 57 pages.

Lopes-Bastos et al. "Tumour-Endothelial Cell Communications: Important and Indispensable Mediators of Tumour Angiogenesis" Anticancer Research Mar. 2016, 36 (3) 1119-1126.

Malakhov et al. "Assessment of Efficacy of Non-Invasive Peripheral Transcutaneous Electrical Nerve Stimulation for Correction of Blood Pressure in Patients With Arterial Hypertension" Journal of Hypertension: Jul. 2019—vol. 37—Issue—p. e88-e89 doi: 10.1097/01.hjh.0000570296.70620.44.

Maltese et al. "The Putative Role of the Antiageing Protein Klotho in Cardiovascular and Renal Disease" Hindawi Publishing Corporation International Journal of Hypertension, (Sep. 2011) vol. 2012, Article ID 757469, 5 pages.

Mann, "Innate Immunity and the Failing Heart: The Cytokine Hypothesis Revisited," Circ. Res. Mar. 27, 2015; 116(7):1254-1268.

Mao et al. "13-Hydrogel fibrous scaffolds for accelerated wound healing" In Woodhead Publishing Series in Biomaterials, Electrofluidodynamic Technologies (EFDTs) for Biomaterials and Medical Devices, Woodhead Publishing, (Jan. 2018) pp. 251-274, ISBN 9780081017456, https://doi.org/10.1016/B978-0-08-101745-6.00013-X.

Martin "Historically significant events in the discovery of RANK/RANKL/OPG" World J Orthop. Oct. 18, 2013; 4(4): 186-197. doi: 10.5312/wjo.v4.i4.186.

Mass Device "Greatbatch wins FDA PMA for Algovita SCS" http://www.massdevice.com/greatbatch-wins-fda-pma-for-algovita-scs/ (Dec. 1, 2015).

Matsumori, "Cytokines and Heart Failure: Pathophysiological Roles and Therapeutic Implications," Heart Failure, Springer, Tokyo; doi.org/10.1007/978-4-431-68331-5_3.

McBride et al. "Aortic valve decalcification" J Thorac Cardiovasc Surg. Jul. 1990; 100(1 ):36-42; discussion 42-3 (Abstract Only).

McGrath "OPG/RANKL/RANK Pathway as a Therapeutic Target in Cancer" Journal of Thoracic Oncology, Sep. 2011 6(9): 1468-1473.

McLean et al., "Training the Biofilm Generation—a Tribute to J. W. Costerton," Journal of Bacteriology, vol. 194, (Dec. 2012), pp. 6706-6711.

McMillan "Longevity Protein' Enables Muscle Regeneration In Old Mice" accesses Jun. 2, 2021; https://www.forbes.com/sites/fionamcmillan/2018/11/25/longevity-protein-enables-muscle-regeneration-in-old-mice/?sh=51709d57392a.

Meadows et al. "Anti-VEGF Therapies in the Clinic," Cold Spring Harb. Perspect. Med. Oct. 2012; 2(10): a006577: doi: 10.1101/cshperspect.a006577.

Medtronic "Cardiac Resynchronization Therapy (CRT) Devices For Heart Failure" http://www.medtronic.com/us-en/patients/treatments-therapies/crt-devices.html.

Mei al. "Combined effect of rhTGF-ß1 and rhPDGF-BB on the expression of Pyk2 protein and mRNA gene during orthodontic tooth movement in SD rats" Shanghai Kou Qiang Yi Xue. Oct. 2019;28(5):472-477. Chinese. PMID: 32274476.

Messas et al. "Feasibility and Performance of Noninvasive Ultrasound Therapy in Patients With Severe Symptomatic Aortic Valve Stenosis: A First-in-Human Study. Circulation" Mar. 2, 2021;143(9):968-970. doi: 10.1161/CIRCULATIONAHA.120.050672. Epub Jan. 25, 2021.

Metro News "Bioelectricity: A shocking revolution in skincare?" Website accessed Aug. 4, 2021 https://metro.co.uk/2010/09/26/bioelectricity-a-shocking-revolution-in-skincare-523763/.

Miles et al. "Assessment of the changes in arch perimeter and irregularity in the mandibular arch during initial alignment with the AcceleDent Aura appliance vs no appliance in adolescents: A single-blind randomized clinical trial", Dec. 2016, vol. 150, Issue 6 American Journal of Orthodontics and Dentofacial Orthopedics (9 pages).

Miron "The Concept of Smart Tissue Regeneration with PRF" (Apr. 3, 2017) accessed Aug. 4, 2021 http://oasisdiscussions.ca/2017/04/03/prf/.

Mishra "Angiogenic neovessels promote tissue hypoxia," Proc. Natl. Acad. Sci. U. S. A. Sep. 20, 2016; 113(38):10458-10460, published online Sep. 13, 2016; doi: 10.1073/pnas.1612427113.

Moe, "Klotho: A Master Regulator of Cardiovascular Disease?," Circulation, vol. 125, (2012), pp. 2181-2183.

Mosteiro et al. "Tissue damage and senescence provide critical signals for cellular reprogramming in vivo." Science, 2016; 354 (6315): aaf4445 DOI: 10.1126/science.aaf4445.

Muratori et al. "The cytotoxic synergy of nanosecond electric pulses and low temperature leads to apoptosis" Sci Rep 6, 36835 (2016). https://doi.org/10.1038/srep36835.

Nacopolous "Use of Platelet Rich Fibrin in Facial Aesthetics and Rejuvenation" (Jun. 2017) accessed Aug. 4, 2021 https://doi.org/10.1002/9781119406792.ch 13.

Nature "Skin regeneration with insights" Nature 551, 141 (Nov. 2017) https://doi.org/10.1038/551141a.

Niiranen et al., "Relative Contributions of Arterial Stiffness and Hypertension to Cardiovascular Disease: The Framingham Heart Study," Journal of the American Heart Association, vol. 5, No. 11, 2016, 8 pages.

Nimeri et al. "Acceleration of tooth movement during orthodontic treatment—a frontier in Orthodontics", Prog Orthod 2013; 14:42; DOI: 10.1186/2196-1042-14-42.

Nodzo et al., "Cathodic Electrical Stimulation Combined With Vancomycin Enhances Treatment of Methicillin-Resistant *Staphylococcus aureus* Implant-Associated Infections," Clinical Orthopaedics and Related Research, vol. 473, (2015), pp. 2856-2864.

Nodzo et al., "Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), 1668-1675.

Nordstorm "Electrical Stimulation Blood Pressure Treatment Devices Market to Set Astonishing Growth by 2026" Art. Apr. 4, 2019 Gator Ledger.

Norton et al. "Bioelectric Perturbations of Bone: Research Directions and Clinical Applications" Angle Orthod (1984) 54 (1): 73-87.

Novack "Inflammatory osteoclasts, a different breed of bone eaters?" Arthritis Rheumatol. Dec. 2016; 68(12):2834-2836. doi: 10.1002/art 39835.

Novickij et al., "Induction of Different Sensitization Patterns of MRSA to Antibiotics Using Electroporation," Molecules, vol. 23, (2018), Article 1799, 10 pages.

O'Neill et al., "Recent Progress in the Treatment of Vascular Calcification," Kidney International, vol. 78, (Dec. 2010), pp. 1232-1239.

Odell et al. "Anti-inflammatory Effects of Electronic Signal Treatment" Pain physician. 11. 891-907 (2008). 10.36076/ppj.2008/11/891.

(56) References Cited

OTHER PUBLICATIONS

Ojeh et al. "Stem Cells in Skin Regeneration, Wound Healing, and Their Clinical Applications" Int. J. Mol. Sci. (Oct. 2015), 16, ISSN 1422-0067 www.mdpi.com/journal/ijms.

Oranger et al. "Cellular Mechanisms of Multiple Myeloma Bone Disease" Clinical and Developmental Immunology vol. 2013, Article ID 289458, 11 pages http://dx.doi.org/10.1155/2013/289458.

Otero et al. "Expression and Presence of OPG and RANKL mRNA and Protein in Human Periodontal Ligament with Orthodontic Force", Gene-Regulation-and-Systems-Biology, 2016, 10 , 15-20.

Our Approach to Improve Hair Loss by Increasing Hair Growth Factor IGF-1, http://www.jhgc.com.sg/theory/igf-1/index.html, visited Mar. 15, 2017.

Oyajobi "Multiple myeloma/hypercalcemia" Arthritis Research & Therapy vol. 9, Article No. S4 (2007).

Palza et al., "Electroactive Smart Polymers for Biomedical Applications," Materials, vol. 12, (2019), 24 pages.

Fukuoka et al., "The Latest Advance in Hair Regeneration Therapy Using Proteins Secreted by Adipose-Derived Stem Cells" The American Journal of Cosmetic Surgery, 29(4):273-282 (2012).

Gavira et al. "Repealed implantation of skeletal myoblast in a swine model of chronic myocardial infarction," Eur. Heart J., 31(8): 1013-1021. doi: 10.1093/eurheartj/ehp342 (2010).

Ge et al. "The aging skin microenvironment dictates stem cell behavior" PNAS (Mar. 2020), vol. 117, No. 10, pp. 5339-5350.

Ghazalian et al. "Effects of whole-body vibration training on fibrinolytic and coagulative factors in healthy young men." Journal of Research in Medical Sciences: the official journal of Isfahan University of Medical Sciences vol. 19,10 (Oct. 2014): 982-986.

Giganti et al. "Changes in serum levels of TNF-alpha, IL-6, OPG, RANKL and their conelation with radiographic and clinical assessment in fragility fractures and high energy fractures", J Biol Regul Homeost Agents, Oct.-Dec. 2012;26(4):671-80.

Giladi et al., "Microbial Growth Inhibition by Alternating Electric Fields," Antimicrobial Agents and Chemotherapy, vol. 52, (2008), pp. 3517-3522.

Golberg et al., "Eradication of Multidrug-Resistant A. Baumannii in Burn Wounds by Antiseptic Pulsed Electric Field," Technology, vol. 2, (2014), pp. 153-160.

Golberg et al., "Pulsed Electric Fields For Burn Wound Disinfection in a Murine Model," Journal of Burn Care & Research, vol. 36, (2015), pp. 7-13.

Goldberg et al. "Skin Rejuvenation with Non-Invasive Pulsed Electric Fields" Sci Rep 5, 10187 (May 2015).

Goranov et al. "Bone Lesions in Multiple Myeloma—The OPG/RANK-ligand System" Folia Med (Plovdiv). 2004; 46(3): 5-11 (Abstract Only).

Goswami et al. "Osteoprotegerin rich tumor microenvironment: implications in breast cancer" Oncotargel. Jul. 5, 2016; 7(27):42777-42791.

Grad, D., "Electrical Scalp Device Can Slow Progression of Deadly Brain Tumors", New York Times, https://www.nytimes.com/2014/11/16/health/electrical-scalp-device-can-slow-progression-of-deadly-brain-tumors.html? r=0(Nov. 15, 2014).

Greenwald "Pulse pressure and arterial elasticity" QJM: An International Journal of Medicine, vol. 95, Issue 2, 2002, pp. 107-112.

Guimaraes-Camboa et al. "Redox Paradox: Can Hypoxia Heal Ischemic Hearts?" Cell, 39(4):392-394, (Nov. 21, 2016) DOI: http://dx.doi.org/10.1016/j.devcel.2016.11.007.

Gullestad et al. "Inflammatory cytokines in heart failure: mediators and markers," Cardiology. 2012;122(1):23-35. doi: 10.1159/000338166. Epub Jun. 12, 2012.

Gurbax et al. "Accelerated Orthodontic Tooth Movement: A Review" mod Res Dent. 1 (2). MRD.000508. 2017. DOI: 10.31031/MRD .2017.01.000508.

Hair Growth Factors, Nanogen, http://www.svijet-kose.com/dokumenti/Serum-vegf.pdf, copyright 2010.

Hamman, R. "Modulation Of RANKL and Osteoprotegerin in Adolescents Using Orthodontic Forces", Masters Thesis, University of Tennessee (2010).

Hamzelou et al. "Cancer reversed in frogs by hacking cells' electricity with light," New Scientist This Week, Mar. 16, 2016.

Hari et al., "Application of Bioelectric Effect to Reduce the Antibiotic Resistance of Subgingival Plaque Biofilm: An in Vitro Study," Journal of Indian Society of Periodontology, vol. 22, (2018), pp. 133-139.

Harkins et al., "Chitosan-Cellulose Composite for Wound Dressing Material. Part 2. Antimicrobial Activity, Blood Absorption Ability, and Biocompatibility," Journal of Biomedical Materials Research Part B, Applied biomaterials, vol. 102, (2014), 1199-1206.

Hart, "RANKL and Osteoprotegerin Levels in Response to Orthodontic Forces" (2012). Theses and Dissertations (ETD). Paper 107. http://dx.doi.org/10.21007/etd.cghs.2012.0127.

HealthCMI, "Acupuncture Combats Hypertension In University of California Research," Available online at < https://www.healthcmi.com/Acupuncture-Continuing-Education-News/1688-acupuncture-c . . . >, (2016), 9 pages.

HealthCMI, "Acupuncture Controls Hypertension In Groundbreaking Trial," Available online at < https://www.healthcmi.com/Acupuncture-Continuing-Education-News/1804-acupuncture-c . . . >, (2017), 9 pages.

HealthCMI, "UC Irvine—Acupuncture Reduces Hypertension Confirmed," Available Online at <https://www.healthcmi.com/Acupuncture-Continuing-Education-News/1792-uc-irvine-acup . . . >, (2017), 6 pages.

Heart Valve Calcifications-Focused Ultrasound TherapyFocused Ultrasound Therapy; Research Paper Last Updated: Jan. 28, 2020, The Focused Ultrasound Foundation Newsletier (5 pages).

Hearts build new muscle with this simple protein patch, jacobsschool.ucsd.edu/news/news releases/release.sfe?id=1813 (Sep. 16, 2015).

Hoffmann, "Regeneration of the gastric mucosa and its glands from stem cells", Curr Med Chem, 15(29):3133-44 (2008).

Holding et al. "The correlation of RANK, RANKL and TNFa expression with bone loss volume and polyethylene wear debris around hip implants" Biomaterials 27(30):5212-9—Nov. 2006.

Holen et al. Role of Osteoprotegerin (OPG) in Cancer Clin Sci (Lond). Mar. 2006; 110(3):279-91. doi: 10.1042/CS20050175.

Hopkins Medicine "Overview of Pacemakers and Implantable Cardioverter Defibrillators (ICDs)," hopkinsmedicine.org/healthlibrary/conditions/cardiovascular_diseases/ )verview of pacemakers and implantable cardioverter defibrillators icds 85,P00234/, last visited Sep. 12, 2018.

Horsburgh et al "MicroRNAs in the skin; role in development, homeostasis, and regeneration" Clin Sci (Lond) (Jul.-Aug. 2017) 131 (15): 1923-1940.

https://www.dicardiology.com/content/bioleonhardt-unveils-stem-pump Jan. 28, 2014.

Hu et al. "Exosomes derived from human adipose mesenchymal stem cells accelerates cutaneous wound healing via optimizing the characteristics of fibroblasts", Nature Scientific Reports, vol. 6, Article No. 32993 (2016).

Hu et al. "Klotho Deficiency Causes Vascular Calcification in Chronic Kidney Disease" J Am Soc Nephrol. Jan. 2011;22(1): 124-136.

Hu Klein, "Vagus Nerve Stimulation: A new approach to reduce heart failure" Cardiology Journal (2010).

Huang et al. "Myocardial transfection of hypoxia-inducible factor-1a and co-transplantation of mesenchymal stem cells enhance cardiac repair in rats with experimental myocardial infarction", Stem Cell Research & Therapy 5:22 (2014) DOI: 10.1186/scrt410.

Hudson et al. "Local delivery of recombinant osteoprotegerin enhances postorthodontic tooth stability" Calcif Tissue Int. Apr. 2012; 90(4):330-42. doi: 10.1007/S00223-012-9579-4.

Hunckler et al. "A current affair: electrotherapy in wound healing" Journal of Multidisciplinary Healthcare (Apr. 2017)10 179-194.

Hy et al., "Insulin-like growth factor 1 and hair growth," Dermatol Online J,; 5(2):1 (Nov. 1999).

Iglesias-Linares et al. "The use of gene therapy vs. corticotomy surgery in accelerating orthodontic tooth movement." Orthod Craniofac Res. Aug. 2011; 14(3):138-48. doi: 10.1111/j.1601-6343.2011.01519. x.

(56) References Cited

OTHER PUBLICATIONS

Infante et al. "RANKL/RANK/OPG system beyond bone remodeling: involvement in breast cancer and clinical perspectives" Journal of Experimental & Clinical Cancer Research (2019) 38:12. https://doi.0rg/10.1186/s13046-018-1001-2.
Interesting study about prolactin, VEGF and angiogenic inhibition, http://www.regrowth.com/hair-loss-forums/topic/interest1ng-study-about-prolactin-vegf-and-angiogenic-inhibition/ (Nov. 2000).
International Search Report for International Application No. PCT/US19/52288, dated Jan. 10, 2020, 11 pages.
International Written Opinion for International Application No. PCT/US19/52288, dated Jan. 10, 2020, 07 pages.
Involvement of hepatocyte growth factor/scatter factor and Met receptor signaling in hair follicle morphogenesis and cycling, FASEB J Feb. 2000 14:319-332.
Israeli innovation uses nerve stimulation to treat heart failure https://www.israel21c.org/israeli-innovation-uses-nerve-stimulation-to-treat-heart-failure/ (Feb. 11, 2007).
Istanbullu et al., "Electrochemical Biofilm Control: Mechanism of Action," Biofouling, vol. 28, (2012), pp. 769-778.
Itatani et al. "Resistance to Anti-Angiogenic Therapy in Cancer-Alterations to Anti-VEGF Pathway" Int J Mol Sci. Apr. 18, 2018;19(4):1232. doi: 10.3390/ijms19041232. PMID: 29670046; PMCID: PMC5979390.
Ivanyi "How Microcurrent Treatments Improve Acne" Envision Acne & Skin Care Center, website accessed Aug. 4, 2021, https://envisionacnecenter.com/microcurrent-treatments-improve-acne/.
Park et al. "Effects of SM-215 on Hair Growth by Hair Follicle Stimulation", Indian Journal of Science and Technology, vol. 8(25), DOI: 10.17485/ijst/2015/v8i25/80263, (Oct. 2015).
Park, Alice "Shrinking Stem Cells Are the Real Reason for Hair Loss" Time, (Feb. 5, 2016).
Paulus "Cytokines and heart failure," Heart Fail. Manit. 2000; 1(2):50-6.
Payne et al. "Bioelectric Control of Metastasis in Solid Tumors" Bioelectricityvol. 1, No. 3, (Sep. 16, 2019) https://doi.org/10.1089/bioe.2019.0013.
Petrescu et al. "Platelet rich fibrin as a gingival tissue regeneration enhancer" Journal of Dental Sciences, https://doi.org/10.1016/j.jds.2020.08.014.
Petrusca et al. "Experimental investigation of thermal effects in HIFU-based external valvuloplasty with a non-spherical transducer, using high-resolution MR thermometry" Phys Med Biol. Sep. 7, 2009;54(17):5123-38. doi: 10.1088/0031-9155/54/17/004. Epub Aug. 6, 2009 (Abstract).
Pierce et al. "Collection and characterization of amniotic fluid from scheduled C-section deliveries," Cell Tissue Bank, DOI 10.1007/s10561-016-9572-7 (Springer, 2012) and is available from Irvine Scientific.
Plumbing Today, "How to Remove Hard, White Mineral Deposits from Faucets/Showerheads," (available at https://plumbingtoday.biz/blog/how-to-remove-hard-white-mineral-deposits-from-faucets-showerheads), (Jul. 11, 2016), 4 pages.
Pozo et al., "Bioelectric Effect and Bacterial Biofilms. A Systematic Review," The International Journal of Artificial Organs, vol. 31, (2008), pp. 786-795.
Pozo et al., "Effect of Electrical Current on the Activities of Antimicrobial Agents Against Pseudomonas Aeruginosa, *Staphylococcus aureus*, and *Staphylococcus epidermidis* Biofilms," Antimicrobial Agents and Chemotherapy, vol. 53, (2009), pp. 35/\0.
Pozo et al., "Prevention of *Staphylococcus epidermidis* Biofilm Formation Using Electrical Current," Journal of Applied Biomaterials & Functional Materials, vol. 12, (2014), pp. 81-83.
Pozo et al., "The Electricidal Effect: Reduction of *Staphylococcus* and Pseudomonas Biofilms by Prolonged Exposure to Low-Intensity Electrical Current," Antimicrobial Agents and Chemotherapy, vol. 53, (2009), pp. 41-45.
Price et al. "Mitral Valve Repair is Feasible Following Extensive Decalcification and Reconstruction of the Atrioventricular Groove" J Heart Valve Dis. Jan. 2015; 24(1):46-52 (Abstract Only).

Prochazka et al. "Therapeutic Potential of Adipose-Derived Therapeutic Factor Concentrate for Treating Critical Limb Ischemia," Cell Transplantation, 25(9), pp. 1623-1633(11) (2016).
Pupo et al., Electrotherapy on Cancer: Experiment and Mathematical Modeling, Current Cancer Treatment—Novel Beyond Conventional Approaches, Prof. Oner Ozdemir (Ed.) ISBN: 978-953-307-397-2, InTech, Available from: http://www.intechopen.com/books/current-cancer-treatment-novel-beyond-conventional-approaches/electrotherapy-on-cancer-experiment-and-mathematical-modeling, 2011.
Puro et al. "Bioelectric impact of pathological angiogenesis on vascular function," PNAS Aug. 30, 2016 113 (35) 9934-9939; published ahead of print Aug. 22, 2016 https://doi.org/10.1073/pnas.1604757113.
Rachner et al. "Prognostic Value of RANKL/OPG Serum Levels and Disseminated Tumor Cells in Nonmetastatic Breast Cancer" Clin Cancer Res Feb. 15, 2019 (25) (4) 1369-1378; DOI: 10.1158/1078-0432.CCR-18-2482.
Raje et al. "Role of the RANK/RANKL Pathway in Multiple Myeloma" Clin Cancer Res 2019 25(1): 12-20; DOI:10.1158/1078-0432.CCR-18-1537.
Ren et al., "Efficient Eradication of Mature Pseudomonas Aeruginosa Biofilm via Controlled Delivery of Nitric Oxide Combined with Antimicrobial Peptide and Antibiotics," Frontiers in Microbiology, vol. 7, Article 1260, (Aug. 2016), 8 pages.
Reversing Age-Related Hair Loss and Restoring Healthy Hair Growth in Men and Women https://nutritionreview.org/2015/08/reversing-age-related-hair-loss-and-restoring-healthy-hair-growth-in-men-and-vomen/ (Aug. 24, 2015).
RFA (radiofrequency ablation), Swedish Medical Imaging, 2 pages, author unknown, undated.
Rocha et al. "Ultrasensitive System for Electrophysiology of Cancer Cell Populations: A Review" Bioelectricityvol. 1, No. 3 (Published Online:Sep. 16, 2019) https://doi.org/10.1089/bioe.2019.0020.
Ronchetti et al. "Dermal alterations in patients with Wilson's disease treated with D-penicillamine" J Submicrosc Cytol Pathol (Jan. 1989) 21(1 ):131-9.
Roy et al., "Disposable Patterned Electroceutical Dressing (PED-10) Is Safe for Treatment of Open Clinical Chronic Wounds," Advances in Wound Care, vol. 8, (1019), pp. 149-159.
Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).
Sabino-Carvalho et al., "Non-invasive Vagus Nerve Stimulation Acutely Improves Blood Pressure Control in a Placebo Controlled Study," The FASEB Journal, vol. 31, 2017, available online at < https://www.fasebj.org/doi/abs/10.1096/fasebj.31.1_supplement.848.8 >, 2 pages) Abstract Only.
Sahmeddini et al., "Electro-Acupuncture Stimulation at Acupoints Reduced the Severity of Hypotension During Anesthesia in Patients Undergoing Liver Transplantation," Journal of Acupuncture and Meridian Studies, vol. 5, Issue 1, (2012), pp. 11-14.
Sahoo and Losardo, "Exosomes and Cardiac Repair After Myocardial Infarction", Circulation Research, 114:333-344 (Jan. 16, 2014).
Sandvik et al., "Direct Electric Current Treatment under Physiologic Saline Conditions Kills *Staphylococcus epidermidis* Biofilms via Electrolytic Generation of Hypochlorous Acid," PloS one, vol. 8, (Feb. 2013), e55118, 14 pages.
Santos et al. "Interferential electrical stimulation improves peripheral vasodilatation in healthy individuals" Braz J Phys Ther. May-Jun. 2013; 17(3):281-288.
Sartori et al. "Effects of Transcutaneous Electrical Nerve Stimulation in Autonomic Nervous System of Hypertensive Patients: A Randomized Controlled Trial" Current Hypertension Reviews, Apr. 2018, 14, 66-71.
Schardong et al., "Intradialytic neuromuscular electrical stimulation reduces DNA damage in chronic kidney failure patients: a randomized controlled trial," Biomarkers, vol. 23, Issue 5, 2018, pp. 1-11.
Schimmel et al. "Neuroinflammation in traumatic brain injury: A chronic response to an acute injury" Brain Circ, 2017, 3(3):135-142.
Schmidt-Malan et al., "Activity of Fixed Direct Electrical Current in Experimental *Staphylococcus aureus* Foreign-Body Osteomyelitis," Diagnostic Microbiology and Infectious Disease, vol. 93, (2019), pp. 92-95.

(56) References Cited

OTHER PUBLICATIONS

Segura et al. "New Material Developed for Accelerated Skin Regeneration in Major Wounds" National Institute of Biomedical Imaging and Bioengineering (Dec. 2015) Accessed Aug. 4, 2021 https://www.newswise.com/articles/new-material-developed-for-accelerated-skin-regeneration-in-major-wounds?channel=.

Seifi & Jeszri "Correlation of bone resorption induced by orthodontic tooth movement and expression of RANKL in rats". Dental Journal, vol. 26, No. 4 (2009).

Sethi et al. "Aortic stiffness: pathophysiology, clinical implications, and approach to treatment" Integr Blood Press Control. 2014; 7: 29-34.

Shahid et al., "Rhinosinusitis in Children," ISRN Otolaryngology, vol. 2012, Article ID 851831, (Dec. 2012), 11 pages.

Shimamura et al. "OPG/RANKL/RANK axis is a critical inflammatory signaling system in ischemic brain in mice." Proceedings of the National Academy of Sciences of the United States of America vol. 111,22 (2014): 8191-6. doi: 10.1073/pnas.1400544111.

Shirtliff et al., "Assessment of the Ability of the Bioelectric Effect to Eliminate Mixed-Species Biofilms," Applied and Environmental Microbiology, vol. 71, (2005), pp. 6379-6382.

Shoji-Matsunaga et al. "Osteocyte regulation of orthodontic force-mediated tooth movement via RANKL expression" Scientific Reports, 7: 8753, published online Aug. 18, 2017, DOI:10.1038/s41598-017-09326-7.

Showkatbakhsh et al. "Effect of Intra-Canal Direct Current Electric Stimulation on Orthodontic Tooth Movement: An Experimental Study in Canines" Journal of Dental School 2016; 34(3): 157-67.

Showkatbakhsh et al. "The effect of pulsed electromagnetic fields on the acceleration of tooth movement." World J Orthod. 2010 Winter;11(4):e52-6.

Signature Orthodontics "Accelerated Tooth Movement", http://www.sigortho.com/accelerated-tooth-movement, visited Mar. 15, 2017.

Silva et al. "Engineered hydrogel-based matrices for skin wound healing" (Dec. 2016) In book: Wound Healing Biomaterials (pp. 227-250) DOI:10.1016/B978-1-78242-456-7.00011-8.

Silvers et al. "The Bioelectric Code: Reprogramming Cancer and Aging from the Interface of Mechanical and Chemical Microenvironments," Front. Cell Dev. Biol., Mar. 6, 2018; doi.org/10.3389/fcell.2018.00021.

Singh et al. "3D Printing of Scaffold for Cells Delivery: Advances in Skin Tissue Engineering" Polymers (Jan. 2016), 8, 19; doi:10/3390/polym8010019.

Sisay et al. "The RANK/RANKL/OPG system in tumorigenesis and metastasis of cancer stem cell: potential targets for anticancer therapy" Onco Targets Ther. 2017; 10: 3801-3810.

Skardal "Amniotic Fluid Stem Cells for Wound Healing" Perinatal Stem Cells (Jul. 2014) Springer, New York, NY. https://doi.org/10.1007/978-1-4939-1118-9_2.

Skardal et al. "Bioprinted Amniotic Fluid-Derived Stem Cells Accelerate Healing of Large Skin Wounds" Stem Cells TranslationalMedicine (Oct. 2012)1:792-802.

Chang et al. Effect of Pulse-Burst Electromagnetic Field Stimulation on Osteoblast Cell Activities; Bioelectromagnetics 25:457-465 (2004).

Chemet & Levin, "Transmembrane voltage potential is an essential cellular parameter for the detection and control of tumor development in a Xenopus model," Dis. Models & Mech. 6, pp. 595-607 (2013); doi: 10.1242/dmm.010835.

Chen et al. "Secreted Klotho Attenuates Inflammation-Associated Aortic Valve Fibrosis in Senescence-Accelerated Mice P1" Hypertension. 2018;71:877-885. DOI: 10.1161/HYPERTENSIONAHA.117.10560.) Downloaded from http://ahajournals.org by on Apr. 24, 2020 (9 pages).

Chen et al. "Beyond anti-VEGF: dual-targeting antiangiogenic and antiproliferative therapy" Am J Transl Res. 2013;5(4):393-403 Published May 24, 2013.

Chen et al. "Nanosecond Pulsed Electric Field (nsPEF) Ablation as an Alternative or Adjunct to Surgery for Treatment of Cancer" Chen et al., Surgery Curr Res 2013, S12 DOI: 10.4172/2161-1076.S12-005.

Chen et al., "Deficiency in the Anti-Aging Gene Klotho Promotes Aortic Valve Fibrosis Through AMPK(Alpha)-Mediated Activation of RUNX2," Aging Cell, vol. 15, (Oct. 2016), pp. 853-860.

Chen et al., "Regenerative Hair Waves in Aging Mice and Extra-Follicular Modulators Follistatin, Dkk1, and Sfrp4," Journal of Investigative Dermatology, Aug. 2014, vol. 134, Issue 8, pp. 2086-2096.

Chen et al., "The Role and Mechanism of (Alpha)-Klotho in the Calcification of Rat Aortic Vascular Smooth Muscle Cells," BioMed Research International, vol. 2015, (2015), 7 pages.

Chen et al., Efficacy and Safety of Acupuncture for Essential Hypertension: A Meta-Analysis, Medical Science Monitor, vol. 24, (2018), pp. 2946-2969.

Chiang et al., "Silver-Palladium Surfaces Inhibit Biofilm Formation," Applied and Environmental Microbiology, vol. 75, (2009), pp. 1674-1678.

Choi et al. "Exosomes from human adipose-derived stem cells promote proliferation and migration of skin fibroblasts" Experimental Dermatology. (Sep. 2017) 1-3.

Christouls et al. "Pathogenesis and Management of Myeloma Bone Disease" Expert Rev Hematol. 2009; 2(4):385-398.

Ciria et al., Antitumor effectiveness of different amounts of electrical charge in Ehrlich and fibrosarcoma Sa-37 tumors, BMC Cancer, Nov. 26, 2004, 10 pages, vol. 4, No. 87.

Collette et al., "Measurement of the local aortic stiffness by a non-invasive bioelectrical impedance technique," in Medical & Biological Engineering, vol. 49, No. 4, Feb. 2011, pp. 431-439, Available online at < https://www.ncbi.nlm.nih.gov/pubmed/21286830>, 1 page (Abstract Only).

Collins "Bioelectric Signals Can Be Used to Detect Early Cancer," Tufts News, http://now.tufts.edu/news-releases/bioelectric-signals-used-detect-early-cancer (Feb. 1, 2013).

Columbia "Implant Procedure Concepts—Pacemaker, ICD and CRT Overview", http://www.columbia.edu/itc/hs/medical/hickey/docs/Pacemaker,%20ICD%20and%20CRT%20Overview%20022007.pdf, copyright 2007.

Control of Hair Growth by a Growth Factor Protein, http://www.hairloss-reversible.com/control-of-hair-growth-by-a-growth-factor-protein, visited Mar. 15, 2017.

Control of pelage hair follicle development and cycling by complex interactions between follistatin and activin, FASEB (Jan. 2, 2003).

Corrigan et al. "Neurogenic inflammation after traumatic brain injury and its potentiation of classical inflammation". Journal of Neuroinflammation, 2016, 13:264; doi://doi.org/10.1186/s12974-016-0738-9.

Costa et al. "Selecting patients for cytotoxic therapies in gastroenteropancreatic neuroendocrine tumours" Best Pract Res Clin Gastroenterol. Dec. 2012;26(6):843-54. doi: 10.1016/j.bpg.2012.12.001. PMID: 23582923.

Costa et al. "Treatment of advanced hepatocellular carcinoma with very low levels of amplitude-modulated electromagnetic fields" Br J Cancer. Aug. 23, 2011;105(5):640-8. doi: 10.1038/bjc.2011.292. Epub Aug. 9, 2011. PMID: 21829195; PMCID: PMC3188936.

Costerton et al., "Mechanism of Electrical Enhancement of Efficacy of Antibiotics in Killing Biofilm Bacteria," Antimicrobial Agents and Chemotherapy, vol. 38, (1994), pp. 2803-2809.

Costerton et al., "The Application of Biofilm Science to the Study and Control of Chronic Bacterial Infections," The Journal of Clinical Investigation, vol. 112, (2003), pp. 1466-1477.

Cowburn et al. "HIF isoforms in the skin differentially regulate systemic arterial pressure" Proc Natl Acad Sci U S A. Oct. 22, 2013; 110(43): 17570-17575.

Cross et al. "Milk Ejection following Electrical Stimulation of the Pituitary Stalk in Rabbits," Nature 166, 994-995 (Dec. 9, 1950); doi:10.1038/166994b0 (Abstract Only).

Dahm et al. "Decalcification of the aortic valve does not prevent early recalcification" J Heart Valve Dis., 9(1):21-6 (Jan. 2000).

(56) References Cited

OTHER PUBLICATIONS

Dai et al. "Nanosecond Pulsed Electric Fields Enhance the Antitumour Effects of the mTOR Inhibitor Everolimus against Melanoma," Scientific Reports vol. 7, Article No. 39597 (2017).
Delcaru el al., "Microbial Biofilms in Urinary Tract Infections and Prostatitis: Etiology, Pathogenicity, and Combating stralegies," Pathogens, vol. 5, (2016), 12 pages.
Desai et al. "Use of Platelet-Rich Fibrin over Skin Wounds: Modified Secondary Intention Healing" Modified secondary intention healing. J Cutan Aesthet Surg (Jan.-Mar. 2013) vol. 6, pp. 35-37.
Deswal el al. "Cytokines and Cytokine Receptors in Advanced Heart Failure An Analysis of the Cytokine Database from the Vesnarinone Trial (VEST)," Circulation. 2001 ;103:2055-2059;:// doi.org/10.1161/01. CIR. 103.16.2055.
Dibart et al. "Tissue response during Piezocision-assisted tooth movement a histological study in rats", Eur J Orthod (2014) 36 (4);457-464; DOI: https://doi.org/10.1093/ejo/cjt079.
Dietrich et al. "Decalcification of the mitral annulus: surgical experience in 81 patients" Thorac Cardiovasc Surg. Oct. 2006; 54(7):464-7 (Abstract Only).
Dimensija "PRF Injections forPRF Forskin RejuvenationSkin Rejuvenationand Tissueand TissuereGenerationRegeneration" accessed Aug. 4, 2021, https://dimensija.lv/news/prf-injekcijas-adas-atjaunosanai-un-audu-regeneracijai?lang=en.
Duscher et al. "Stem Cells in Wound Healing: The Future of Regenerative Medicine? A Mini-Review" (May 2015) Stem Cells in Wound Healing, Gerontology 2016;62:216-225.
Ehrlich et al., "Engineering Approaches for the Detection and Control of Orthopaedic Biofilm Infections," Clinical Orthopaedics and Related Research, vol. 437, (2005), pp. 59-66.
El-Bialy et al. "Effect of Low Intensity Pulsed Ultrasound (LIPUS) on Tooth Movement and Root Resorption: A Prospective Multi-Center Randomized Controlled Trial" J Clin. Med. 2020, 9, 804; doi:10.3390/jcm9030804.
Elastatropin(Registered) in Scalp & Hair Conditioning https://www.proteingenomics.com/haircare.html, visited Mar. 15, 2017.
Ellis, Marie "Cure for baldness? Stem cells bring hope" http://www.medicalnewstoday.com/articles/271898.php.
Eurekalert, UCI Study Finds Acupuncture Lowers Hypertension by Activating Natural Opioids, Available Online at < https://www.eurekalert.org/pub_releases/2016-10/uoc-usf103116.php >, (2016), 2 pages.
Fallon "The obvious next step in the evolution of natural rejuvenation" Article (Aug. 2017) (accessed Aug. 4, 2021) https://www.newbeauty.com/platelet-rich-fibrin-skin-rejuvenation-prf/.
Fan et al., "A Review on the Nonpharmacological Therapy of Traditional Chinese Medicine with Antihypertensive Effects," Evidence-Based Complementary and Alternative Medicine, vol. 2019, (2019), Article ID 1317842, 7 pages.
FDA "Same Surgical Procedure Exception under 21 CFR 1271. 15(b): Questions and Answers Regarding the Scope of the Exception-Guidance for Industry" U.S. Department of Health and Human Services, Food and Drug Administration, Center for Biologies Evaluation and Research, Nov. 2017.
Ferris, "Battle against baldness turns to stem cells" http://www.cnbc.com/2015/01/29/studies-indicate-its-possible-to-use-stem-cells-to-cure-baldness.html (Jan. 29, 2015).
Ferrucci, D. A. "Introduction to This is Watson'," in IBM Journal of Research and Development, vol. 56, No. 3.4, pp. 1:1-1:15, May-Jun. 2012. DOI: 10.1147/JRD.2012.2184356.
Fili et al. "Therapeutic implications of osteoprotegerin" Cancer Cell International vol. 9, Article No. 26 (2009).
Flachskampf et al., "Randomized Trial of Acupuncture to Lower Blood Pressure," Circulation, vol. 115, (2007), pp. 3121-3129.
Fonseca et al. "Electrical stimulation: Complementary therapy to improve the performance of grafts in bone defects?" Journal of Biomedical Materials Research Part B: Applied Biomaterials 2018 vol. 000b, Issue 0.
Froughreyhani et al., "Effect of Electric Currents on Antibacterial Effect of Chlorhexidine Against Entrococcus Faecalis Biofilm: An in Vitro Study," Journal of Clinical and Experimental Dentistry, vol. 10, (Dec. 2018), pp. e1223-e1229.
Fujiya et al. "Microcurrent Electrical Neuromuscular Stimulation Facilitates Regeneration of Injured Skeletal Muscle in Mice" Journal of Sports Science and Medicine (Jun. 2015) 14, 297-303.
Fukuoka et al. "Hair Regeneration Treatment Using Adipose-Derived Stem Cell Conditioned Medium: Follow-up With Trichograms" Eplasty, 15:e10 (Mar. 2015).
Witkowski et al. "Klotho—a Common Link in Physiological and Rheumatoid Arthritis-Related Aging of Human CD4+ Lymphocytes" J Immunol (2007), 178(2):771-777; DOI: doi.org/10.4049/jimmunol.178.2.771.
Xia et al. "Klotho Contributes to Pravastatin Effect on Suppressing IL-6 Production in Endothelial Cells." Mediators of Inflammation vol. 2016 (2016): 2193210. doi:10.1155/2016/2193210.
Xie et al. "Klotho Acts as a Tumor Suppressor in Cancers" Jul. 2013 Pathology & Oncology Research 19(4) DOI: 10.1007/S12253-013-9663-8.
Xuan et al. "Changes in expression of klotho affect physiological processes, diseases, and cancer." Iranian journal of basic medical sciences vol. 21,1 (2018): 3-8.
Yaden et al. "Follistatin: a novel therapeutic for the improvement of muscle regeneration," Journal of Pharmacology and Experimental Therapeutics Mar. 13, 2014, jpet.113.211169; DOI: doi.org/10.1124/jpet.113.211169.
Yamauchi et al. "Wound healing delays in a-Klotho-deficient mice that have skin appearance similar to that in aged humans—Study of delayed wound healing mechanism" Biochemical and Biophysical Research Communications vol. 473, Issue 4, May 13, 2016, pp. 845-852.
Yarbrough et al. "Specific binding and mineralization of calcified surfaces by small peptides." Calcified Tissue International vol. 86,1 (2010): 58-66. doi:10.1007/s00223-009-9312-0.
Zhang et al. "Association of Klotho and interleukin 6 gene polymorphisms with aging in Han Chinese population." J Nutr Health Aging. Dec. 2014;18(10):900-4. doi: 10.1007/s12603-014-0470-z. PMID: 25470806.
Zhang et al. "Klotho Protein Protects Human Keratinocytes from UVB-lnduced Damage Possibly by Reducing Expression and Nuclear Translocation of NF-?B." Medical Science Monitor: International Medical Journal of Experimental and Clinical Research vol. 24 8583-8591. Nov. 27, 2018, doi:10.12659/MSM.910687.
Zhao et al. "Enhancing endogenous capacity to repair a stroke-damaged brain: An evolving field for stroke research" Progress in Neurobiology vols. 163-164, Apr.-May 2018, pp. 5-26.
Zhou et al. "Advance of Stem Cell Treatment for Traumatic Brain Injury" Front. Cell. Neurosci., (Aug. 13, 2019): doi.org/10.3389/fncel.2019.00301.
Zhou et al. "Klotho gene deficiency causes salt-sensitive hypertension via monocyte chemotactic protein-1/CC chemokine receptor 2-mediated inflammation" Journal of the American Society of Nephrology : JASN vol. 26,1 (Jan. 2015): 121-32. doi:10.1681/ASN.2013101033.
Zhou et al. "Sonic hedgehog signaling in kidney fibrosis: a master communicator" Science China. Life sciences vol. 59,9 (Sep. 2016): 920-9. doi:10.1007/s11427-016-0020-y.
Ziaaldini et al. "Exercise training increases anabolic and attenuates catabolic and apoptotic processes in aged skeletal muscle of male rats" Exp Gerontol. Jul. 2015; 67:9-14. doi: 10.1016/j.exger.2015.04.008. Epub Apr. 21, 2015. PMID: 25910622.
Zou et al. "The role of klotho in chronic kidney disease." BMC nephrology vol. 19,1 285. Oct. 22, 2018, doi: 10:1186/s12882-018-1094-z.
Zununi et al. "Klotho and Renal Fibrosis," Nephro-Urol Mon. (Nov. 2013) 5(5):946-948. doi: 10.5812/numonthly.16179.

\* cited by examiner

| KLOTHO | OPG | KLOTHO |
|---|---|---|
| 0.649913 | 21.31382 | 2.480879 |
| 496.0868 | 3.083639 | 1.109483 |
| 1.946573 | | |
| 3.416525 | | |
| 1.736225 | | |
| 4.655161 | | |

| KLOTHO | |
|---|---|
| 0.649913 | 11.02667 |
| 1.946573 | 17.3098 |
| 3.416525 | 25.70403 |
| 1.736225 | 26.38801 |
| 4.655161 | 26.14059 |
| 2.480879 | 21.31382 |
| 1.564877 | 6.895227 |
| 0.699834 | 3.083639 |

*FIG. 14*

KIDNEY TREATMENT

CROSS-REFERENCE TO RELATED APPLICATION

The application is a continuation-in-part of U.S. patent application Ser. No. 16/352,756 filed on Mar. 13, 2019, pending, the disclosure of which is hereby incorporated herein in its entirety by this reference.

FIELD

The application relates generally to the field of medical devices and associated treatments, and more specifically to precise bioelectrical stimulation of a subject's muscle tissue, possibly augmented with the administration of a composition comprising, among other things, stem cells and nutrients, useful to stimulate and treat the subject, the subject's kidneys. More specifically, the application relates to a device, programmed bioelectric signaling sequences, and associated methods for the controlled expression of Klotho and other proteins via precise bioelectrical signaling sequences.

BACKGROUND

Klotho protein is a kidney-secreted hormone that is known to be both membrane-bound and secreted. In man, Klotho is associated with muscle regeneration, rejuvenation, and neural protection. Loss of Klotho contributes to the aging-like features of human chronic kidney disease ("CKD") and progression of CKD. Its deficiency is also associated with degenerative processes and accelerated aging.

As found by S. Ranjit et al., "Since Klotho cannot cross the blood brain barrier, it is speculated that there exist two different pools of Klotho, one secreted from kidney into serum and other secreted by the choroid plexus into cerebrospinal fluid. Due to these reasons, therapeutic use of Klotho to provide neuroprotection [to reduce neuroinflammation and oxidative damage] is limited". S. Ranjit et al. "Potential neuroprotective role of astroglial exosomes against smoking-induced oxidative stress and HIV-1 replication in the central nervous system." *Expert Opin Ther Targets*. 2018 August; 22(8):703-714.

Ricardo Ferrari described that the enhanced regenerative response in aged muscle following two weeks of electrical stimulation "Estim" (i.e., a Neuromuscular Stimulator (Empi 300 PV, St Paul, Minn., US)) was associated with a somewhat limited, but still increased expression of Klotho (similar to that achieved from muscle contraction, e.g., exercise). Ricardo Ferrari "The Effect of Electrical Stimulation on Aged Skeletal Muscle Regenerative Potential" http://d-scholarship.pittedu/28094/1/FerrariRJ_ETD_May_31_2016 PDF .pdf.

Findings suggest that Klotho is inversely associated with senescence cells, and that Estim modulates Klotho expression in aged MPCs, and there is precedent to suggest that Klotho plays a role in inhibiting cellular senescence. See also, Dalise et al. "Biological effects of dosing aerobic exercise and neuromuscular electrical stimulation in rats", *Sci Rep.* 2017 Sep. 7; 7(1):10830.

Schardong et al. "Intradialytic neuromuscular electrical stimulation reduces DNA damage in chronic kidney failure patients: a randomized controlled trial", *Biomarkers*, 2018, 23:5,495-501, DOI: 10.1080/1354750X.2018.1452049, described using generic neuromuscular electrical stimulation (LAMES) to reduce DNA damage in patients undergoing hemodialysis. While a step in the right direction, the further benefits of enhanced Klotho expression as described herein are still needed.

BRIEF SUMMARY

Described herein is a bioelectric stimulator particularly configured to activate expression and/or release of Klotho in and from muscle tissue, which is used to treat, e.g., the kidneys. The bioelectric stimulator may be further configured to regulate (e.g., increase) expression and/or release of stromal cell-derived factor 1 ("SDF-1"), vascular endothelial growth factor ("VEGF"), insulin-like growth factor 1 ("IGF-1"), follistatin, receptor activator of nuclear factor kappa-B ligand ("RANKL"), hepatocyte growth factor ("HGF"), endothelial NOS ("eNOS"), tropoelastin, activin A+B, and epidermal growth factor ("EGF"), and any combination thereof.

Also described is a bioelectric stimulator including: a power source (e.g., battery, capacitor, or other suitable source of electricity), and means for delivering an electrical signal to a subject's muscle tissue (e.g., via electrode(s) or wirelessly). The bioelectric stimulator utilizes the electrical signal to precisely control expression of protein(s) in the tissue on demand.

In certain cases, the bioelectric stimulator is programmed to produce a bioelectric signal that stimulates target tissue (e.g., muscle tissue of a subject's thigh) to express and/or release Klotho polypeptide by the target tissue utilizing a bioelectric signal comprising a biphasic square pulse at 20 Hz, 0.1 V (100 mV), and a 7.8 ms pulse duration for, e.g., 30 minutes of stimulation. Typically, stimulation time is about 35 minutes (30 to 40 minutes) twice a week until the kidney improves (e.g., in 8 to 16 weeks.) In certain embodiments, stimulation time of about 15 minutes, once a week for 8 to 24 weeks.

The amount of Klotho expression enhanced by the herein described system is greater than that seen with generic electrical muscle stimulation or muscle contraction alone.

In certain embodiments, non-invasive bioelectric stimulation controlled release of the Klotho protein is used to enhance kidney health in a subject (e.g., treat kidney failure in a subject non-invasively).

In certain cases, the subject has been diagnosed as suffering from kidney failure, diabetes, fibrotic kidney disease, diabetic neuropathy, diabetic nephropathy, lupus nephritis, hypertension-related renal disease, bone degeneration, aging, kidney cancer, polycystic kidney disease, and/or immune system dysfunction. In certain cases, the subject is receiving or has received radiation treatment or chemotherapy for cancer.

A preferred system includes: a bioelectric stimulator that controls/stimulates the release/production of Klotho by a target muscle cell or tissue. The stimulator may be associated with (e.g., connected to) the muscle tissue to express the protein(s) with a pacing infusion lead (available from Nanoscribe of Eggenstein-Leopoldshafen, Germany) or wirelessly.

The stimulator can be designed to externally deliver all regeneration promoting signals wirelessly to the subject's organ(s), tissue(s), and/or cells. In certain embodiments, a micro infusion pump may be included in the system to deliver the proteins described herein or other supportive substances in greater volume more quickly.

While not intending to be bound by theory, the described system utilizes precise bioelectric signaling sequences that appear to communicate with DNA and cell membranes within stimulated tissues of the subject to cause the cells to produce high volumes of, e.g., the Klotho protein, which is released into the circulation, and is useful for, e.g., kidney regeneration and treatment.

BRIEF DESCRIPTION OF THE DRAWINGS

FIG. 14 is a table depicting the results with respect to Klotho.

DETAILED DESCRIPTION

In certain embodiments, described is a bandage wrap that is applied to the affected region. A micro-stimulator may be located conveniently in the bandage wrap and is utilized to distribute specific bioelectric signals to the affected tissue and nerves that regulate various protein expressions for stem cell homing, stem cell proliferation, stem cell differentiation, blood vessel formation, blood circulation improvement, muscle function repair, and DNA repair.

Figure 1:
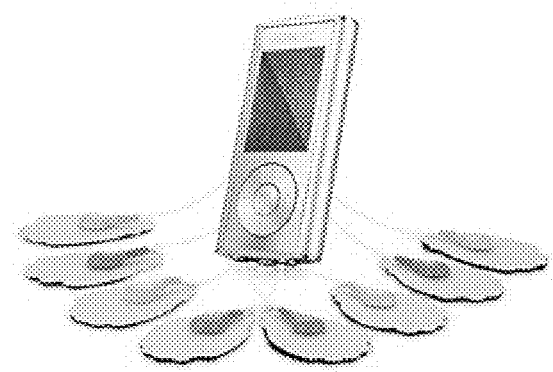
FIG. 1 depicts a programmed bioelectric stimulator for delivery to a subject connected to multiple soft conductive electrode pads.
Figure 2:
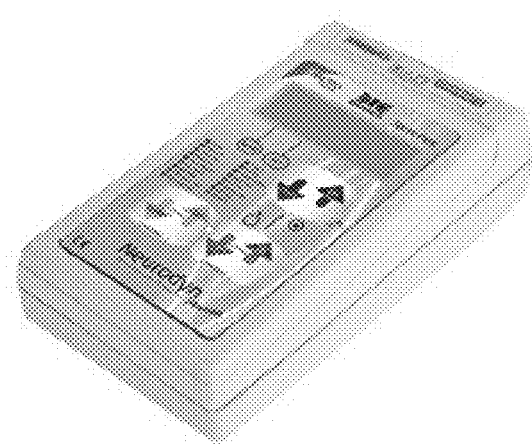
FIG. 2 depicts a programmed bioelectric stimulator as described herein.
Figure 3:
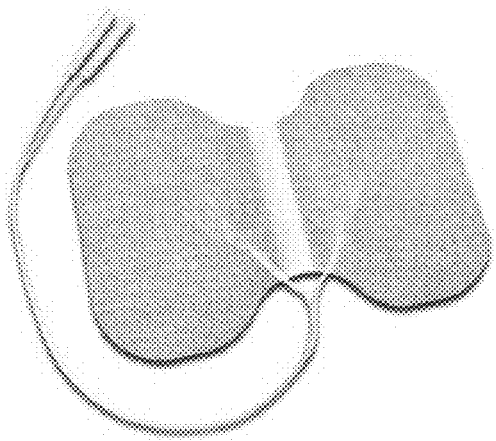
FIG. 3 depicts a conductive soft wrap that may be used with the system.
Figure 4:
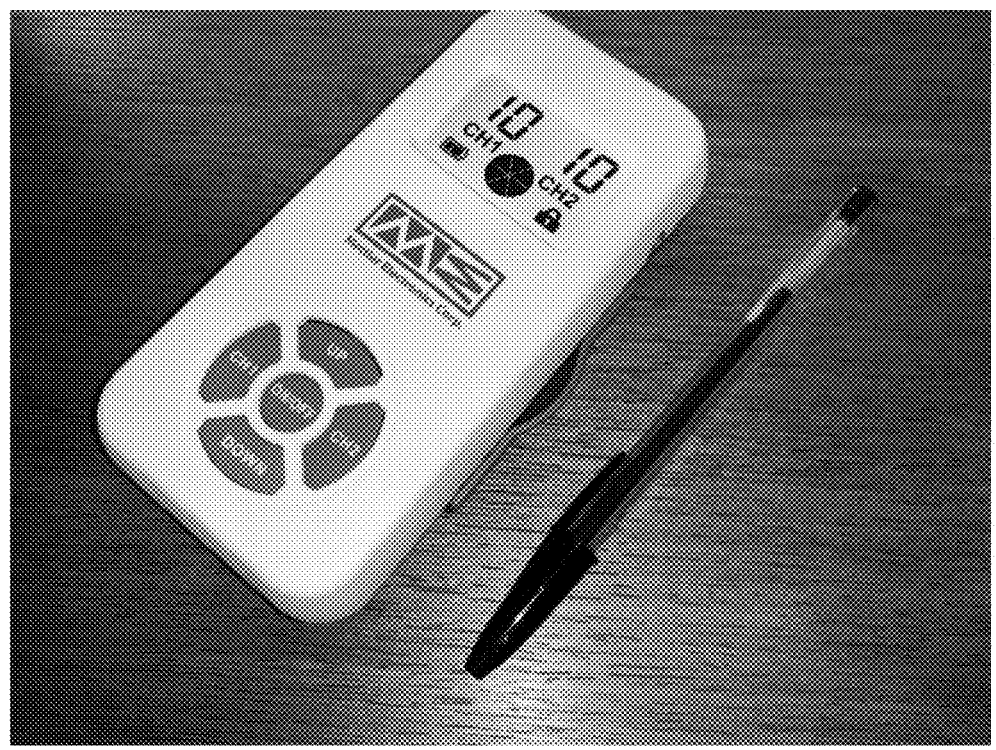
FIG. 4 depicts a programmed bioelectric stimulator depicted alongside a pen.

Referring now to FIG. 1, depicted is a stimulator for use in treating a human. The depicted device is about the size of a pen (FIG. 4) and is programmable.

Preferably, the system utilizes a bioelectric stimulator programmed to control expression and/or release of Klotho, SDF-1, VEGF, IGF-1, follistatin, RANKL, HGF, eNOS, tropoelastin, activin A+B, and/or EGF.

Klotho is as described above.

SDF-1 is a stem cell homing factor that recruits a person's own stem cells to stimulated tissues). US 20180064935A1 to Leonhardt et al., the contents of which are incorporated herein by this reference, depicts in FIG. 17 a bioelectric signal (voltage and frequency) associated with the increased expression of SDF-1: 3.5 mV, 30 Hz, square wave. See, also, FIG. 20 of the incorporated US 20180064935A1 to Leonhardt et al., which depicts a bioelectric signal (voltage and frequency) associated with the increased expression of SDF-1 (2nd part): 0.25 mA (3.0V shown here), 100 Hz, 100 µs pulse width, square wave."

VEGF is for new blood vessel growth. FIG. 19 of the incorporated US 20180064935A1 to Leonhardt et al. a bioelectric signal (voltage and frequency) associated with the increased expression by a cell of VEGF, i.e., 100 mV, 50 Hz, square wave.

IGF-1 is for DNA repair at the level of the cell nucleus. See, e.g., FIG. 6 where a bioelectric signal (voltage and frequency) applied to a cell of 3 mV with electric frequency of 22 Hz, and current of 1 mA for 15 minutes and 3 mA for 15 minutes leads to an increased expression of IGF-1 by the cell.

Figure 5:
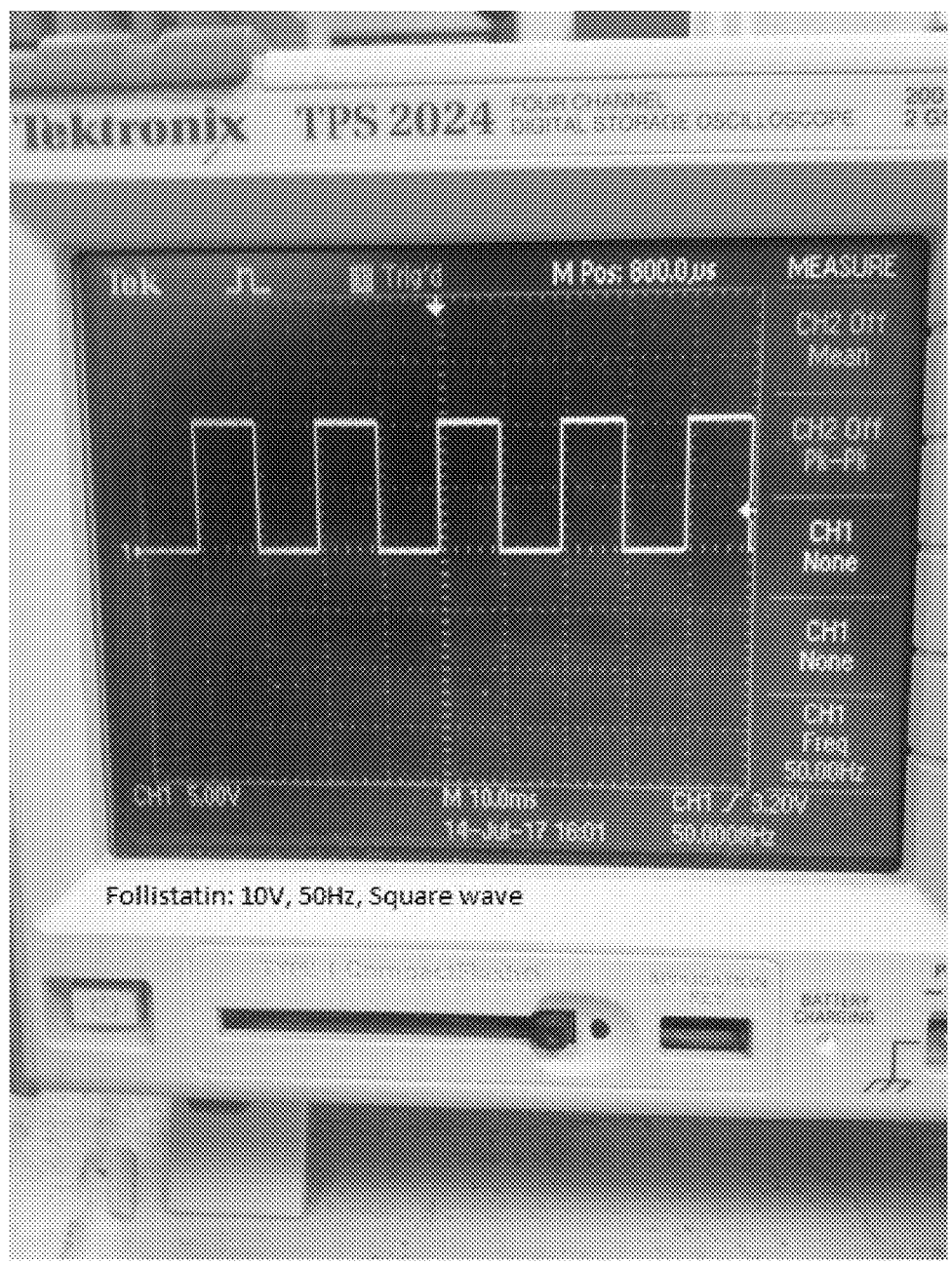
FIG. 5 depicts an image of the signal (voltage and frequency) associated with follistatin at 10V/cm, 50 Hz, square wave.

Follistatin is for, e.g., tissue regeneration. See, e.g., FIG. 5 where a bioelectric signal (voltage and frequency) applied to a cell of 10V/cm, 50 Hz, square wave, leads to an increased expression of follistatin by the cell.

RANKL is for demineralization and tissue loosening (when needed). FIG. 16 of the incorporated US 20180064935A1 to Leonhardt et al. depicts a bioelectric signal (voltage and frequency) associated with the increased expression of RANKL, i.e., 3.0 mV, 2 Hz, square wave." See, also ¶ [00185] of US 20190022389A1 to Leonhardt, the contents of which are incorporated herein by this reference, RANKL/TNF-α, nuclear factor-kappa B (NF-κB) ligand/TNF-α: 3 mV at 2/100 Hz alternating frequency with a current of 3 mA followed by 15 Hz, one (1) Gauss EM field, consisting of 5-millisecond bursts with 5-microsecond pulses followed by 200-µs pulse duration at 30 Hz and with current amplitude of 140 mA.

Figure 9:
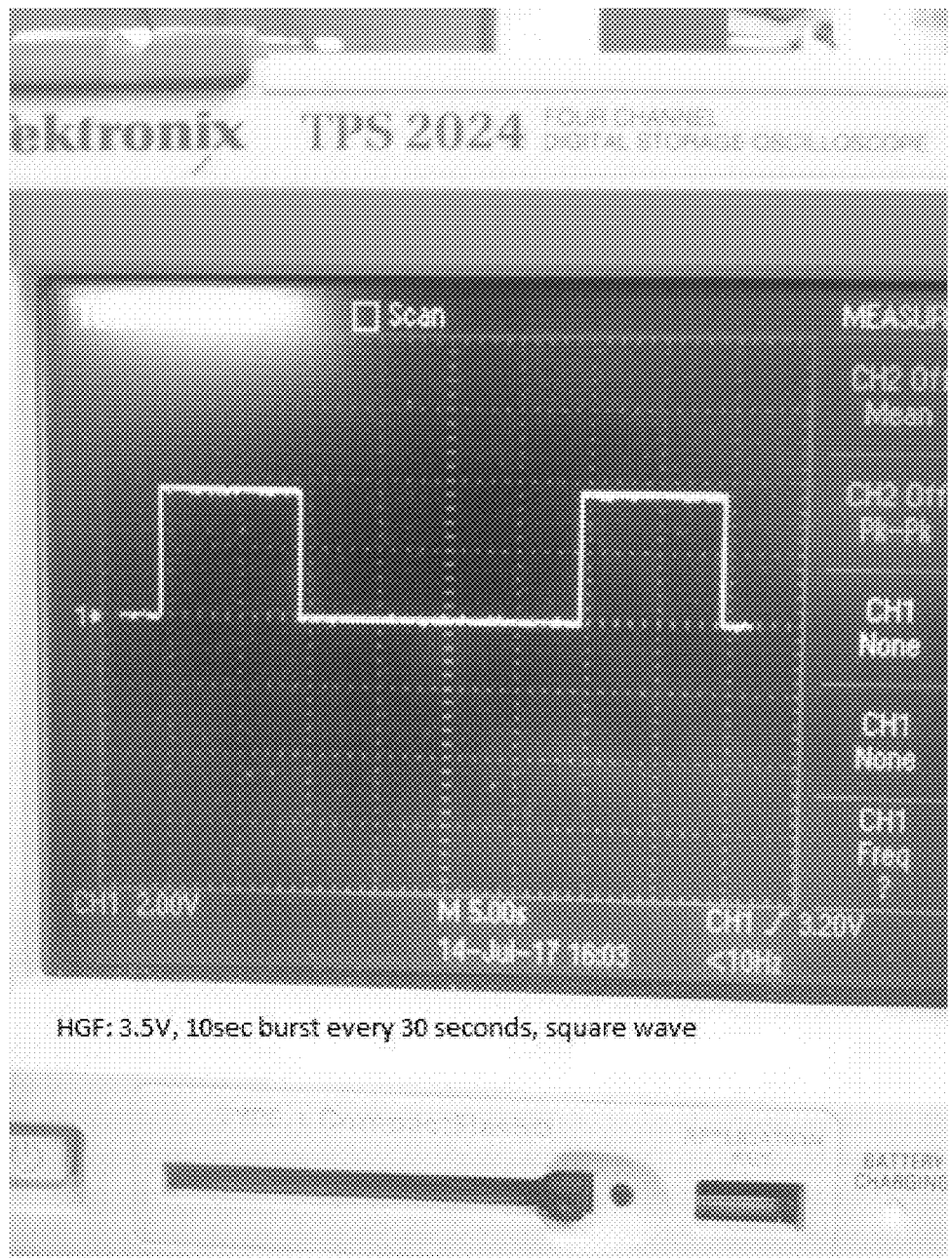
FIG. 9 depicts an image of a signal (voltage and frequency) associated with HGF of 3.5V, 10 second burst every 30 seconds, square wave."

HGF is for tissue regeneration. FIG. 9 of the incorporated US 20180064935A1 to Leonhardt et al. depicts an image of a bioelectric signal (voltage and frequency) associated with the increased expression of HGF at 3.5 V, 10 second burst every 30 seconds, square wave. See, also ¶ [00153] of US 20190022389A1 to Leonhardt, "In such a method, when the electrical signal includes (within 15%): 3.5 V stimulation in 10 second bursts, one (1) burst every 30 seconds at a frequency of about 50 Hz (duration 5 minutes) (wherein the electrical signal is as measured three (3) mm deep into the tissue), the protein produced is HGF."

eNOS is for dilating blood vessels for increasing flow. When bioelectric signal includes (within 15%): alternating high-frequency (HF) and medium-frequency signals (MF), symmetric, biphasic, trapezoid pulses, with 400-µs pulse duration and 1.5/1-s ramp-up/ramp-down duration, respectively (wherein the electrical signal is as measured three (3) mm deep into the tissue), the expression of eNOS increases. ¶ [00186] of the incorporated US 20190022389A1 to Leonhardt also describes alternating high-frequency (HF) and medium-frequency signals (MF): Symmetric, biphasic, trapezoid pulses, with 400-µs pulse duration and 1.5/1-s ramp-up/ramp-down duration, respectively. HF consisted of 75 Hz pulses with 6 second on-21 second off for 15 minutes. MF consisted of 45 Hz pulses with 5 second on-12 second off for 15 minutes. Followed by stimulation duration set as 20 minutes for both one (1) Hz and 20 Hz stimulations. For one (1) Hz stimulation, stimulation is applied for 9 seconds, followed by a one (1) second silent period, a total of 1080 stimulations for 20 min. For 20 Hz stimulation, stimulation is applied for 2 seconds, followed by silent period for 28 seconds, a total of 1600 stimulations for 20 min. Duration 2 minutes.

Tropoelastin increases the elasticity of any tissues and promotes wound healing. Applying 0.06 V with 50 Hz alternating electrical field and electric current of 1 mA for 15 minutes and 3 mA to a cell for 15 minutes increases expression of tropoelastin in the cell. See, also ¶[00234] of the incorporated US 20190022389A1 to Leonhardt, "FIG. 18 [of US 20190022389A1 to Leonhardt] depicts an image of the signal (voltage and frequency) associated with tropoelastin: 60 mV, 50 Hz, square wave."

Figure 6:
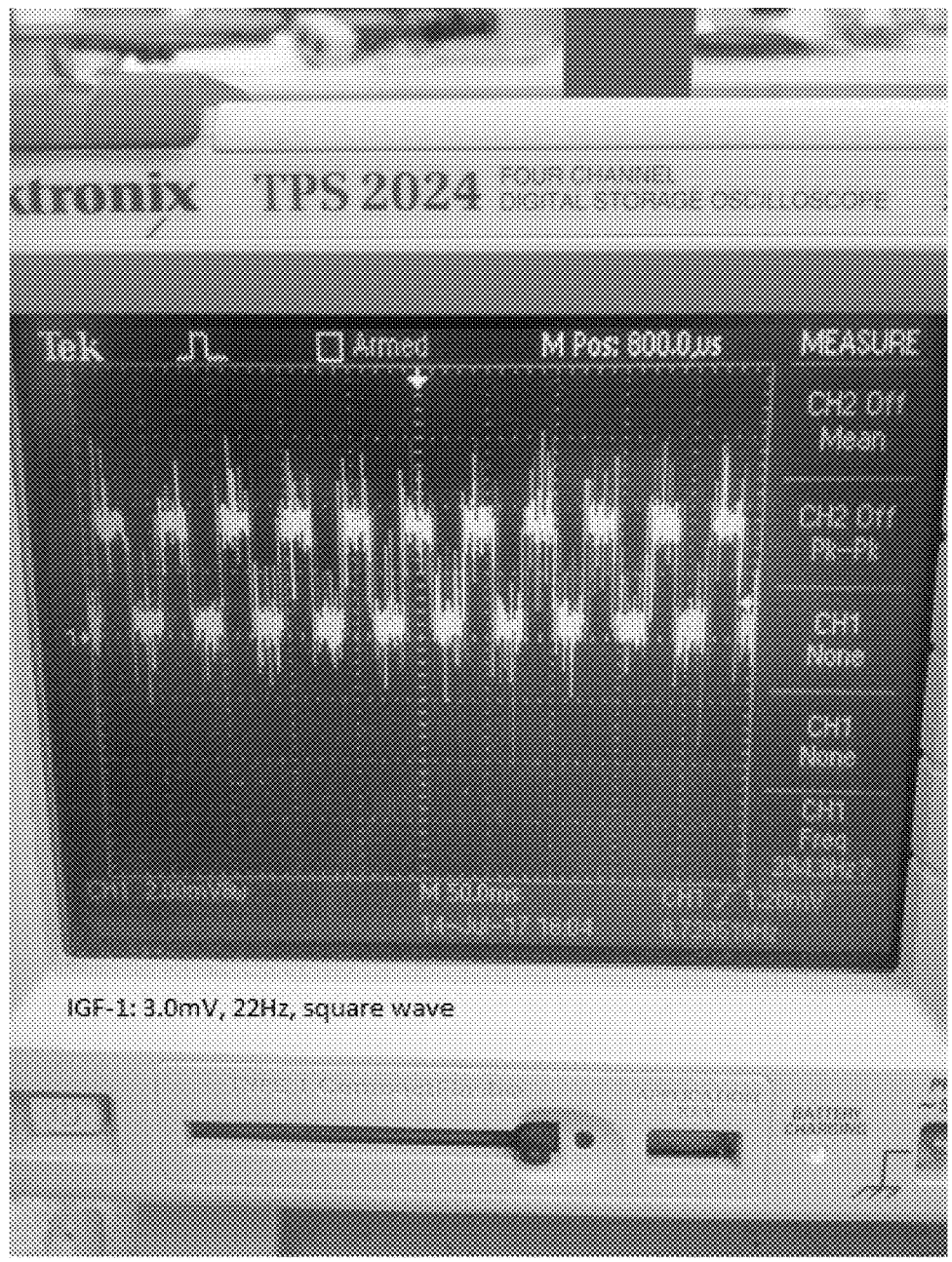
FIG. 6 depicts an image of the signal (voltage and frequency) associated with IGF-1: 3.0 mV, 22 Hz, square wave.

As depicted in FIG. 6 of the incorporated US 20180064935A1 to Leonhardt et al., a bioelectric signal (voltage and frequency) associated with the increased expression of Activin B is at 6.0 mV, pulse width 100 μs, square wave." See, also ¶[00187] of US 20190022389A1 to Leonhardt, "Activin B: 6 mV at 150 Hz Monophasic square wave pulse 0.1 ms in duration current of 15 mA for 15 minutes. Duration 2 minutes.

Figure 7:
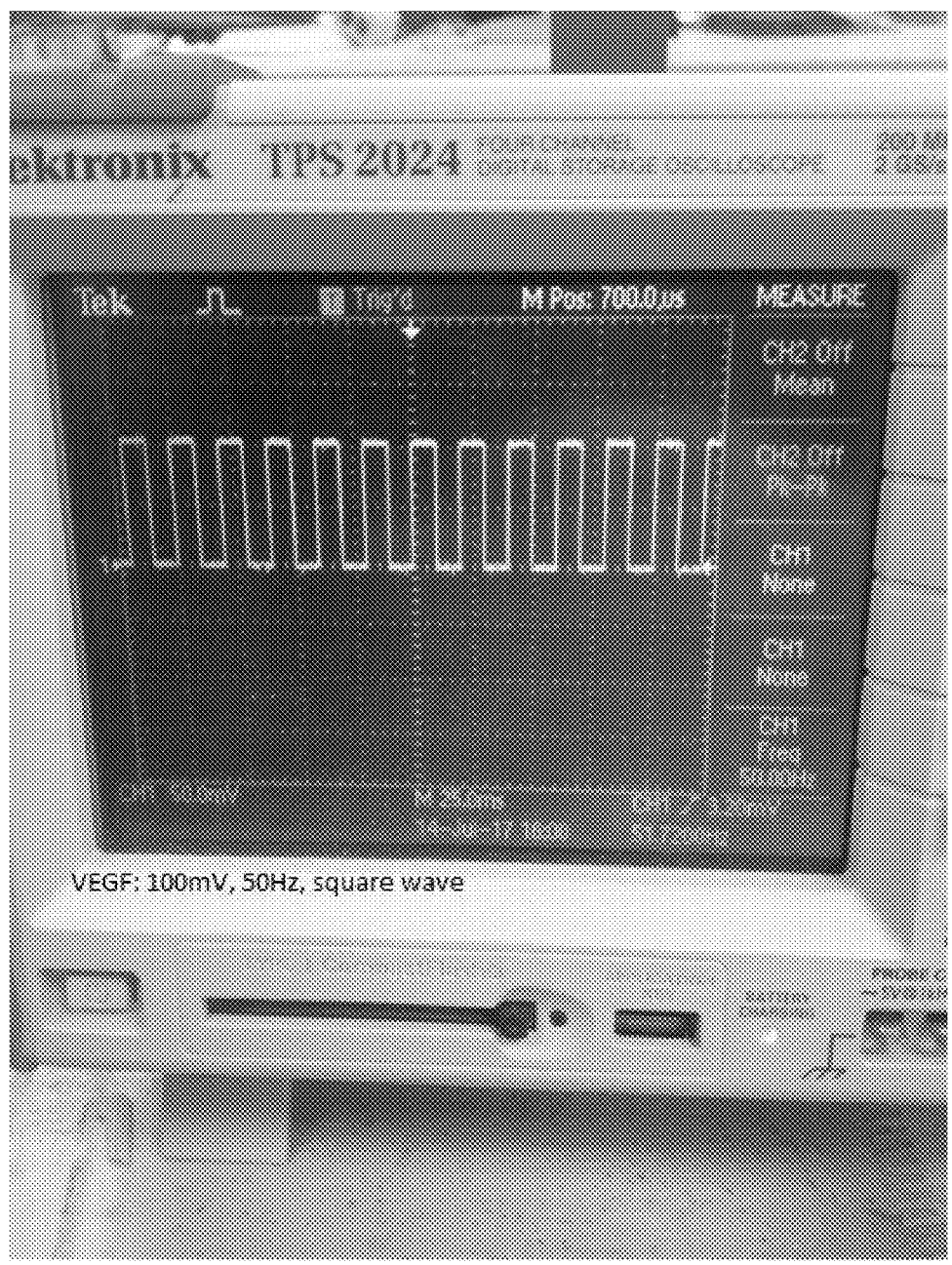
FIG. 7 depicts an image of a signal (voltage and frequency) associated with VEGF and depicts an image of the signal (voltage and frequency) of 100 mV, 50 Hz, square wave."

EGF is used for tissue regeneration. FIG. 7 of the incorporated US 20180064935A1 to Leonhardt et al. depicts an image of a bioelectric signal (voltage and frequency) associated with the increased expression of EGF at 10 V/cm (5 V here), 500 Hz, pulse width 180 μs, square wave. See, also ¶ [00188] of the incorporated US 20190022389A1 to Leonhardt, "EGF—10 V/cm, pulse-width 180 ↕μs, 500 Hz. Duration 9 minutes."

The micro voltage signal generator may be produced utilizing the same techniques used to produce a standard heart pacemaker well known to a person of ordinary skill in the art. An exemplary microvoltage generator is available (for experimental purposes from Cal-X Stars Business Accelerator, Inc. DBA Leonhardt's Launchpads or Leonhardt Vineyards LLC DBA Leonhardt Ventures of Salt Lake City, Utah, US). The primary difference is the special electrical stimulation signals needed to control, e.g., precise follistatin release on demand (which signals are described later herein). The leading pacemaker manufacturers are Medtronic, Boston Scientific Guidant, Abbott St. Jude, BioTronik and Sorin Biomedica.

Construction of the electric signal generators and pacemakers, are known in the art, and can be obtained from OEM suppliers as well as their accompanying chargers and programmers. The electric signal generators are programmed to produce specific signals to lead to specific protein expressions at the right time for, e.g., optimal organ treatment or regeneration.

A pacing infusion lead may be constructed or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

In certain embodiments, the bioelectric stimulator is a micro implantable bioelectric stimulator combined with an implantable re-fillable micro infusion pump with infusion and electrical stimulation catheters. An under the skin micro infusion pump may be re-filled, e.g., daily via a silicone septum with a kidney treatment/regeneration composition comprised of stem cells and support factors.

An infusion and electrode wide area patch may be constructed by cutting conduction polymer to shape, and forming plastic into a flat bag with outlet ports in strategic locations.

In certain embodiments, the interface with the subject's tissue may be by a conductive soft wrap. Gel tape electrodes that come with the Mettler device, which are highly efficient at skin surface delivery, may be used to deliver the bioelectric signal(s). In certain embodiments, electro acupuncture needles may be used to deliver the bioelectric signal(s). Using a Mettler stim unit /TENS device (Mettler Electronics of Anaheim, CA, US) with standard gel tape electrodes automatically calibrates the driving voltage to get through the skin to the target tissues.

Micro stimulators may be purchased or constructed in the same manner heart pacemakers have been made since the 1960's. When used with a micro infusion pump, such pumps can be purchased or produced similar to how they have been produced for drug, insulin, and pain medication delivery since the 1970's. The programming computer can be standard laptop computer. The programming wand customary to wireless programming wands may be used to program heart pacers.

Wireless, non-invasive and/or implantable, wire leads ("electrode") may be used to deliver the regeneration and healing promoting bioelectric signals to target organs.

A wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

Bioelectric stimulation can be done with the described microstimulator, which can have a pacing infusion lead with, e.g., a corkscrew lead placed/attached at, e.g., the center of the tissue to be stimulated and/or treated.

The microstimulator is actuated and runs through programmed signals to signal the release of, e.g., Klotho. In certain embodiments, the bioelectric signal is (within 15%): a biphasic square pulse at 20 Hz, 0.1 V (100 mV), and a 7.8 ms pulse duration for 24 hours of stimulation (wherein the electrical signal is as measured three (3) mm deep into the tissue), the protein expressed and/or released is Klotho.

Also described is a method of activating a tissue to further produce stromal cell-derived factor 1 ("SDF-1"), the method including: stimulating the (e.g., human) tissue with an electrical signal, wherein the electrical signal includes (within 15%): 30 pulses per second with a voltage of about 3.5 mV, and successively alternating currents of about 700 to 1500 picoamps for about one minute, and again with 700 to 1500 picoamps for about one minute and stimulated with current of about 0.25 mA, pulse duration of about 40 pulses/s, pulse width of about 100 μs, wherein the electrical signal is as measured three (3) mm deep into the tissue. In such a method, the period of time is typically at least 24 hours. In such a method, the field strength is typically at least 0.1 V/cm.

In such a method, when the electrical signal includes (within 15%): 3 mv with a frequency of about 22 Hz, and a current of about 1 mA for about fifteen (15) minutes and 3 ma for about fifteen (15) minutes (duration 5 minutes) (wherein the electrical signal is as measured three (3) mm deep into the tissue), the protein further expressed and/or released by the subject is IGF-1.

In such a method, when the electrical signal includes (within 15%): 10V at 50 Hz and 100 Hz for about 12 hours each (duration 1 minute) (wherein the electrical signal is as measured three (3) mm deep into the tissue), the protein further expressed and/or released by the subject is follistatin.

For example, upregulation of IGF-1, and SDF-1 was achieved in cardiomyocytes using such signals. Upregulation of SDF-1 was achieved in pig heart. It has been found that signals for one cellular tissue work with other cellular tissues too.

What follows are preferred signals from the stimulator. The test tissue was sheep heart tissue. The test cells are mesenchymal stem cells.

SDF-1—Stem cell recruiting signal: 30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 µs, and frequency of 100 Hz—each signal for 40 minutes to 8 hours a day for 2 to 36 months as needed for ideal results. Duration 7 minutes.

Stem cell proliferation signals: 15 mV and a current of 500 picoamps at 70 pulses per minute for 3 hours and 20 pulses per minute, a pulse amplitude of from 2.5-6 volts, and a pulse width of from 0.2-0.7 milliseconds for 3 hours. Duration 3 minutes.

Follistatin—(muscle growth) production signal: 10V at 50 HZ and 100 HZ 0.25 mA. Duration 1 minute.

IGF-1: 3 mv with electric frequency of 22 Hz, and electric current of 1 mA for 15 minutes and 3 mA for 15 minutes. Duration 5 minutes.

An exemplary bioelectric signal sequence in humans (after Klotho) is as follows.

SDF-1 (stem cell homing signal)—5 minutes
IGF-1 signal (DNA repair)—3 minutes
Follistatin signal (myostatin antagonist) at 1 volt (not 10 volts)—3 minutes.

A week after treatment, samples can be collected for morphometric evaluation by in-situ hybridization or RT-PCR.

Among the accompanying figures are included images of the corresponding signals with the name, voltage, and frequency of each signal written on each image The signals are to be further defined in terms of current and frequency, not voltage and frequency as shown. The voltage delivered to the cells will be different for each tissue type, but with current all of the signals can be kept constant regardless of tissue type. The device should have a current driven signal (instead of voltage driven like most other devices).

Follistatin is a powerful antagonist of myostatin. Follistatin was first isolated from the ovary and is known to suppress follicle-stimulating hormone. The system has precise bioelectric signaling sequences that have demonstrated an ability to control release of the follistatin protein in target tissue on demand.

Activin A may be produced by a bioelectric signal of 6.0 mV, pulse width 100 µs, square wave, and/or 1.25 V at 5 to 10 Hz frequency. A bioelectric signal to upregulate TGF-β may also be useful in this regard too.

Relationship between the components: The micro voltage signal generator is attached to the pacing infusion lead with, e.g., a corkscrew tip or conductive polymer bandage or patch to the tissue or organ to be treated. An external signal programmer may be used to program the micro voltage signal generator with the proper signals for treatment including the Klotho producing signal. The device battery may be re-chargeable with an external battery charging wand.

The essential elements are the micro voltage signal generator and the means for delivering the signal to the target tissue.

The signal generator may be external or internal. The transmission of the signal may be wireless, via liquid and/or via wires.

The tissue contact interface may be, e.g., a patch or bandage or may be via electrodes or leads. FDA-cleared gel tape electrodes (Mettler) may be used for skin delivery. Electro acupuncture needles may be used to ensure the signals positively reach target tissues under the skin.

In certain embodiments, a subject's organ(s) and/or tissue(s) are first scanned or analyzed with a device to determine what his or her needs may be before treatment begins. The scanning/analysis can be by, e.g., generating mechanical vibrations at position adjacent the location to be an analyzed as described in, e.g., US 2003/0220556 A1 to Porat et al. (the contents of which are incorporated herein by this reference) and/or by measuring transmembrane voltage potential of a cell (see, e.g., Chernet & Levin, "Transmembrane voltage potential is an essential cellular parameter for the detection and control of tumor development in a Xenopus model," Dis. Models & Mech. 6, pp. 595-607 (2013); doi:10.1242/dmm.010835, the contents of which are also incorporated herein by this reference. See, also, Brooks et al. "Bioelectric impedance predicts total body water, blood pressure, and heart rate during hemodialysis in children and adolescents" J. Ren Nutr., 18(3):304-311 (May 2008); doi: 10.1053/j.jrn.2007.11.008, the contents of which are incorporated herein by this reference, describing the use of bioelectric impedance to evaluate the variability of blood pressure, systolic blood pressure, etc.

As used herein, "scanning" means measuring bioelectrical electrical activity of organs, sometimes by placement of a bion coil reader and transmitter in the organ, and direct that information to a computer. The computer stores the bioelectrical read measurements of diseased organs and healthy organs and makes a comparative exam classifying the organ into one category or another, which is much like a doctor using information to make a diagnosis.

Presently, the best approach for whole body and individual organ scanning is to use a combination of: a. 3D Body Scannint, b. Quantum Magnetic Resonance Scanning, c. Biofeedback scanning, d. Bioelectric scanning, e. Bion implant scanning, f Nervous system scanning, and g. Light activated cell reaction reading.

Scanners such as the Ina'Chi scanner, the Quantum Magnetic Resonance Analyzer (QMRA), the 3D Quantum Health Analyzer Scan whole body organ health 2, Body-Scan® scanner, and the "BIONic muscle spindle" are also useful.

For example, the subject is positioned for analysis with a device, preferably with a non-invasive testing device for evaluating, e.g., the autonomic nervous system, organ function(s), and risk factors associated with heart disease, diabetes, and stroke. The non-invasive testing device may analyze data from, e.g., the subject's skin galvanic response, skin color, oximeter, blood pressure, and body composition analyzer to determine hardening and thickening of the subject's arteries, the subject's heart health, exercise capacity, thyroid function, neurotransmitter balance, and multiple other markers for health. See, also, Fatemi et al. "Imaging elastic properties of biological tissues by low-frequency harmonic vibration" *Proceedings of the IEEE*, 91(10):1503 1519 (October 2003).

In an alternative embodiment, the analysis conducted by the device comprises (or further includes) detecting minute energy fields around the human body with, e.g., a "SQUID magnetometer" (SQUID is an acronym for "Superconducting Quantum Interference Device"), able to detect biomagnetic fields associated with physiological activities in the subject's body. A quantum resonant magnetic analyzer analyzes such fields. The magnetic frequency and energy of a subject's organ(s) and/or tissue(s) are collected by appropriately positioning the sensor with respect to the portion of the subject's organ(s) and/or tissue(s) to be analyzed, and after amplification of the signal by the instrument, the data are compared with standard quantum resonant spectrum of diseases, nutrition, and other indicators/markers to determine whether the sample waveforms are irregular using a Fourier approach.

Treatment may include, e.g., moving magnets or changing magnetic fields (pulsed electromagnetic fields) about the tissue and/or organ, for example, to reduce inflammation or treat pain or induce tissue growth in the subject.

The invention is further described with the aid of the following illustrative Example.

EXAMPLES

Example

Controlling Expression and/or Release of Klotho

Twelve samples of gingiva cells were stimulated with a biphasic square pulse at 20 Hz, 0.1 V (100 mV), and a 7.8 ms pulse duration for 24 hours of stimulation. The cells were gingival fibroblasts from a 28 year old Caucasian male (https://www.atcc.org/en/Products/All/CRL-2014.aspx), which were passaged less than 8 times. RT-PCR was used to measure results before and after the described bioelectric stimulation. Results: Klotho expression up an average of 248% (n=5) and as high as 465% (see FIG. 14).

Example

Kidney Treatment

A bioelectric stimulator is programmed to produce Klotho (20 Hz for 30, 0.1 V (100 mV), and a 7.8 ms pulse duration minutes twice a week application) for treatment of a kidney patient. The bioelectric signal is applied to the thigh of the patient. Both the patient's muscles and the patient's kidneys have improved function.

Example

Further Kidney Treatment

Figure 8:
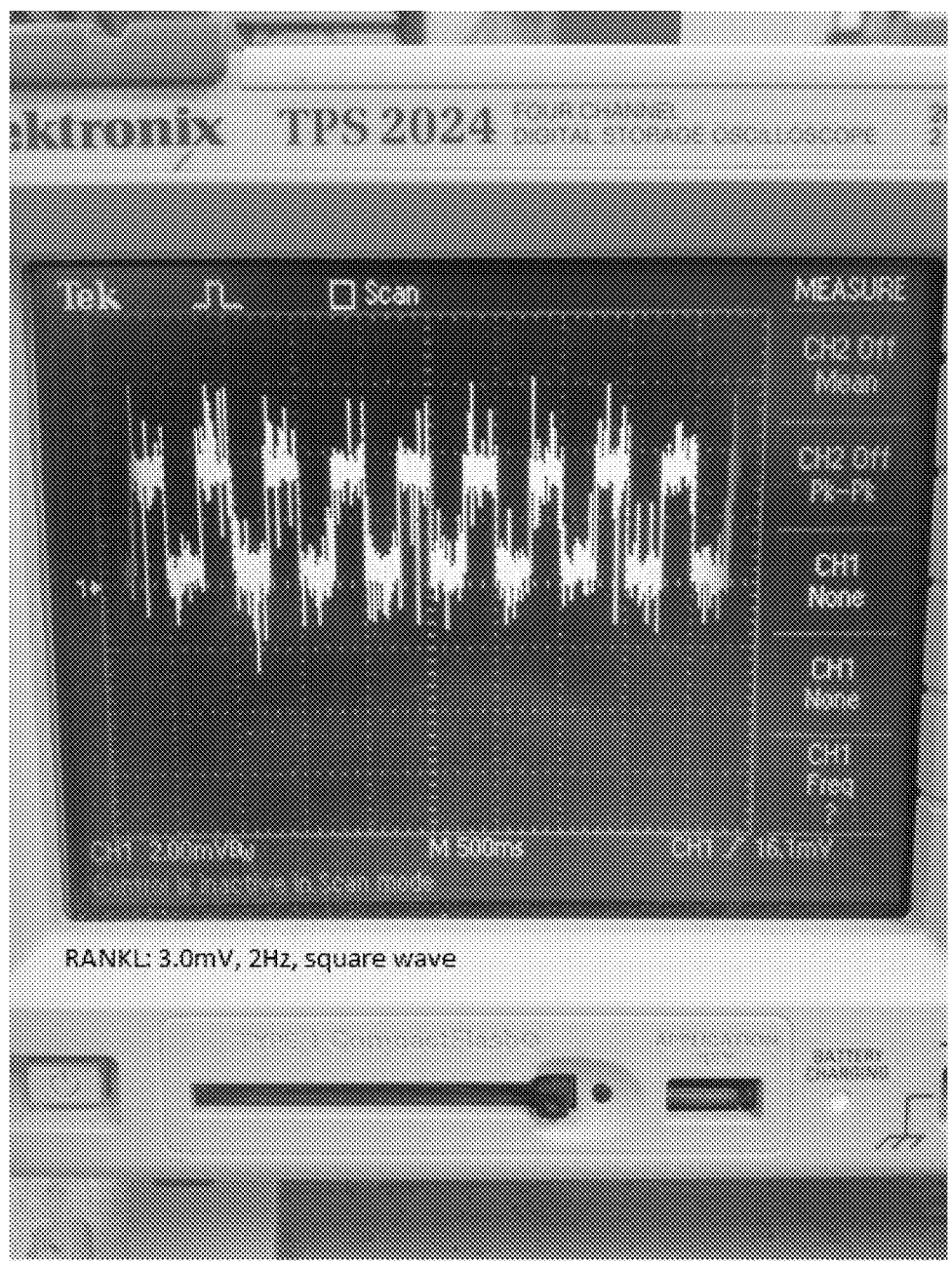
FIG. 8 depicts an image of a signal (voltage and frequency) associated with RANKL and depicts an image of the signal (voltage and frequency) of 3.0 mV, 2 Hz, square wave."
Figure 10:
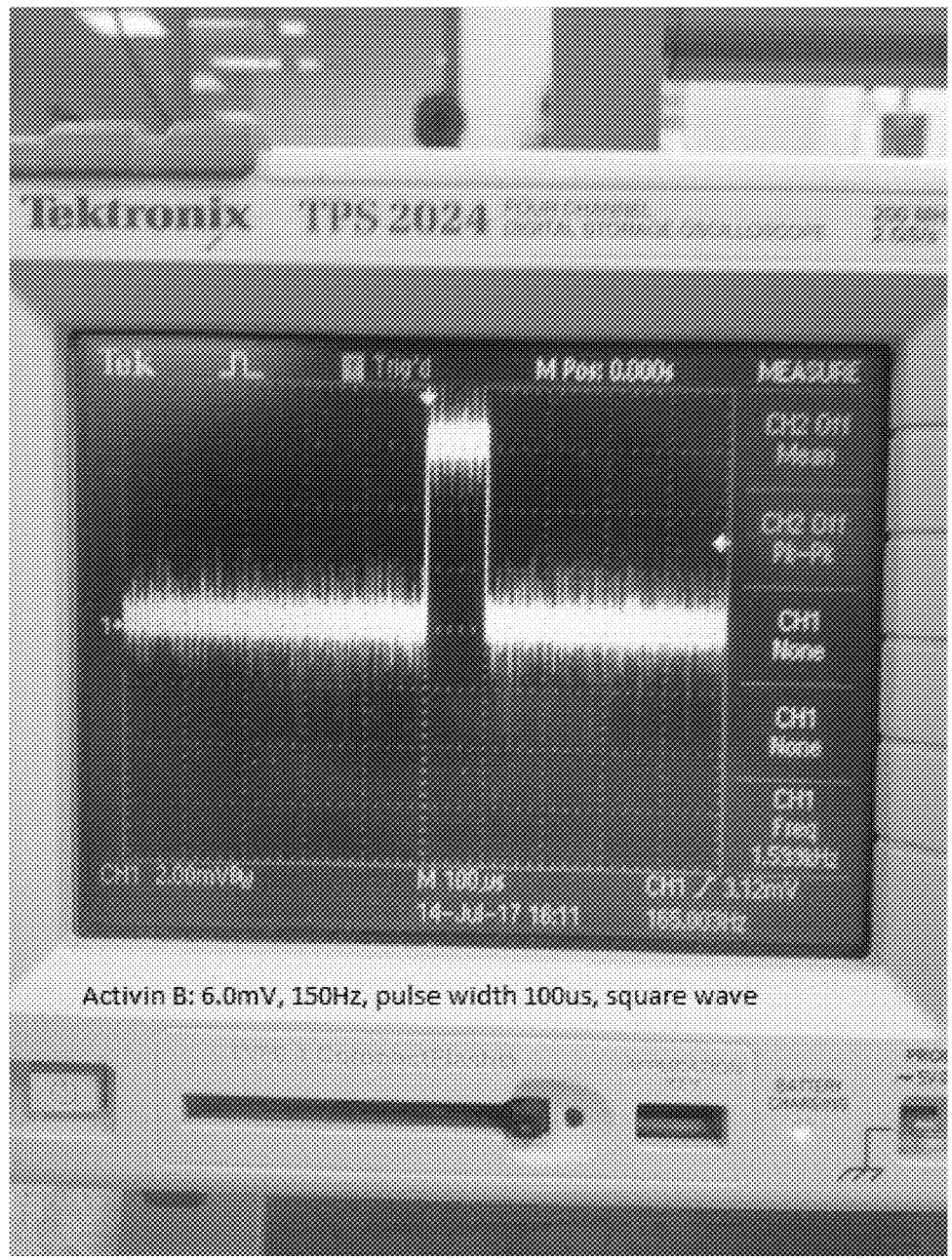
FIG. 10 depicts an image of the signal (voltage and frequency) associated with Activin B of 6.0 mV, pulse width 100 µs, square wave.
Figure 11:
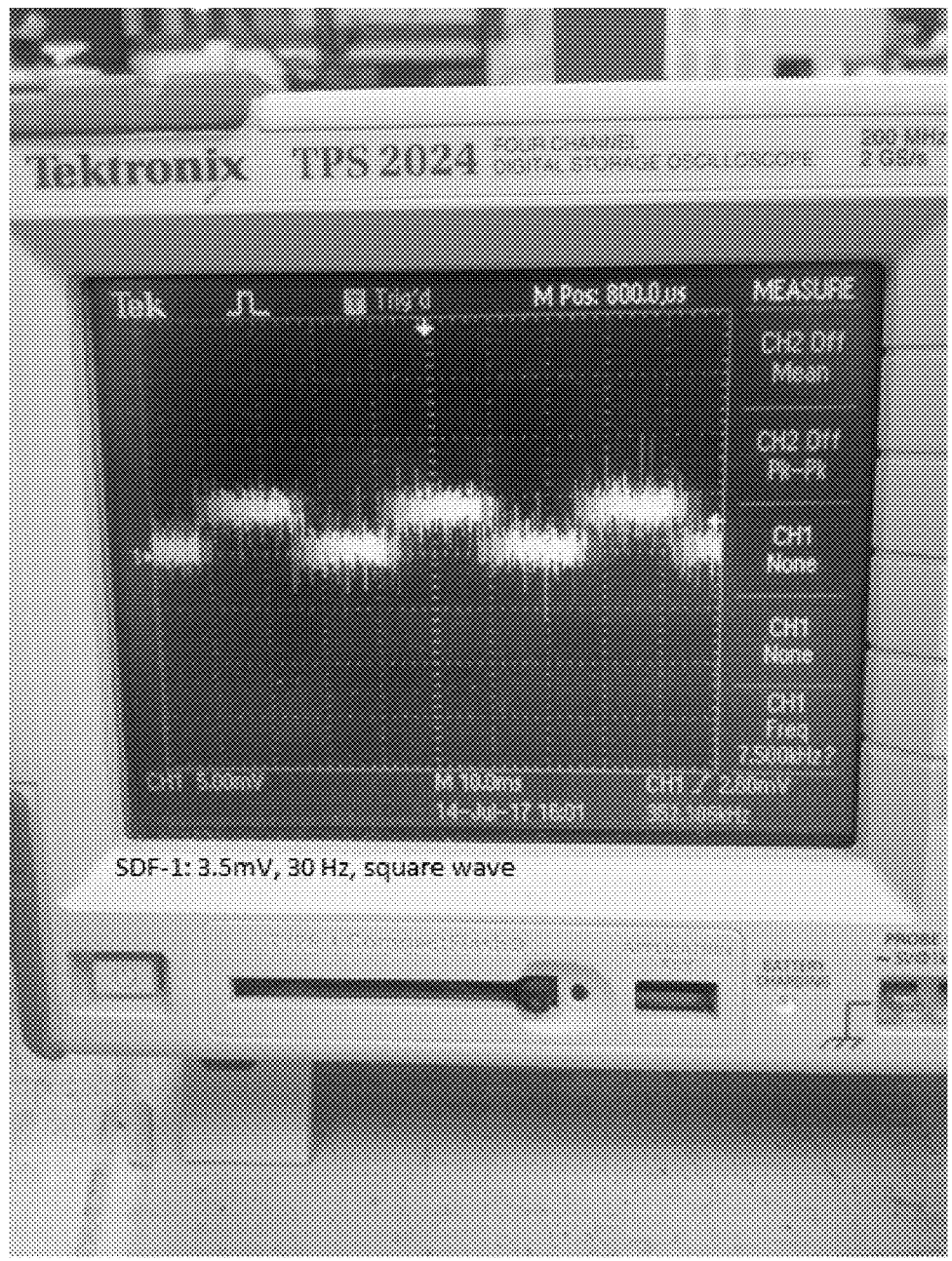
FIG. 11 depicts an image of the signal (voltage and frequency) associated with SDF-1: 3.5 mV, 30 Hz, square wave.
Figure 12:
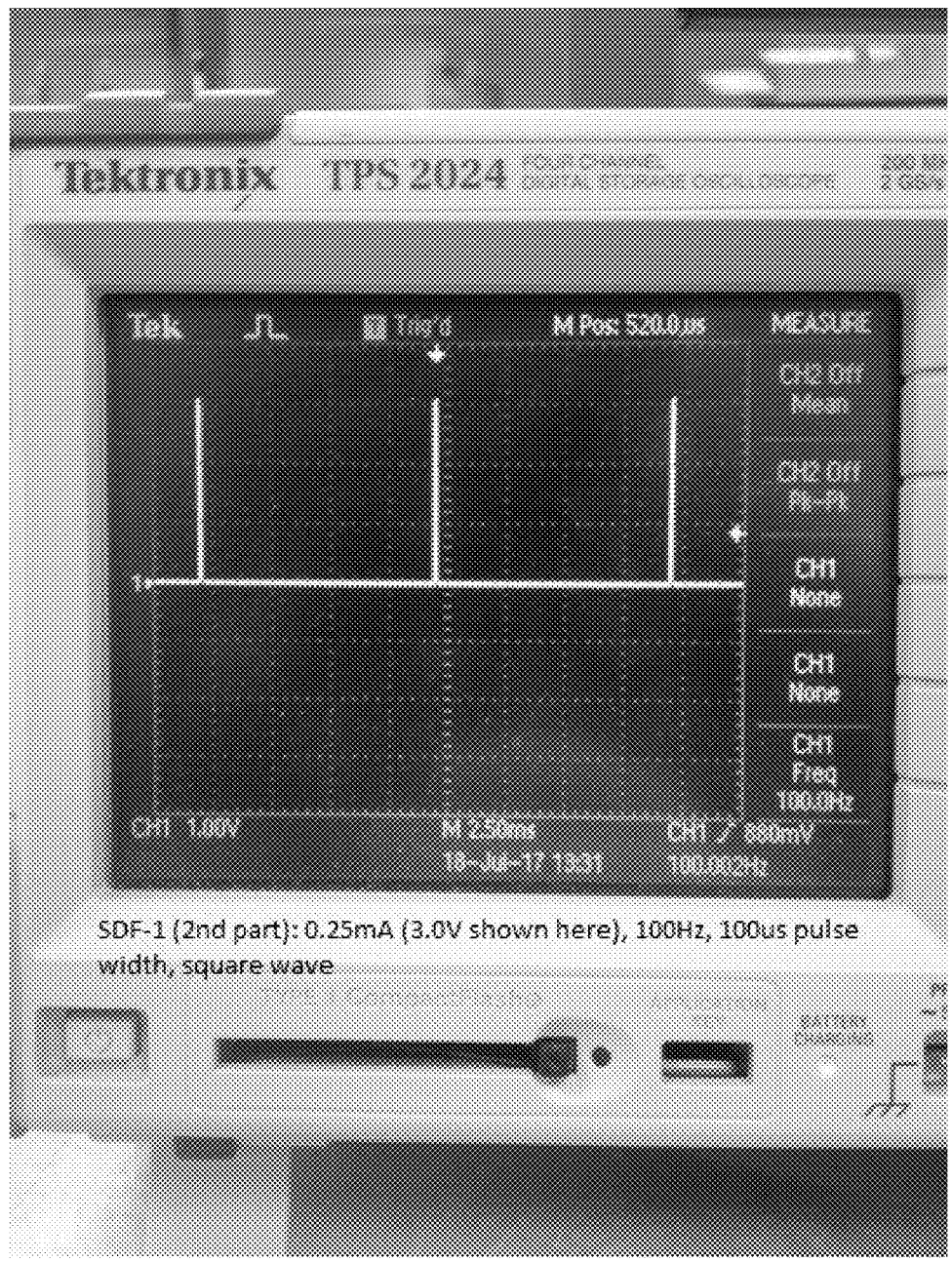
FIG. 12 depicts an image of the signal (voltage and frequency) associated with SDF-1 ($2^{nd}$ part): 0.25 mA (3.0V shown here), 100 Hz, 100 µs pulse width, square wave.
Figure 13:
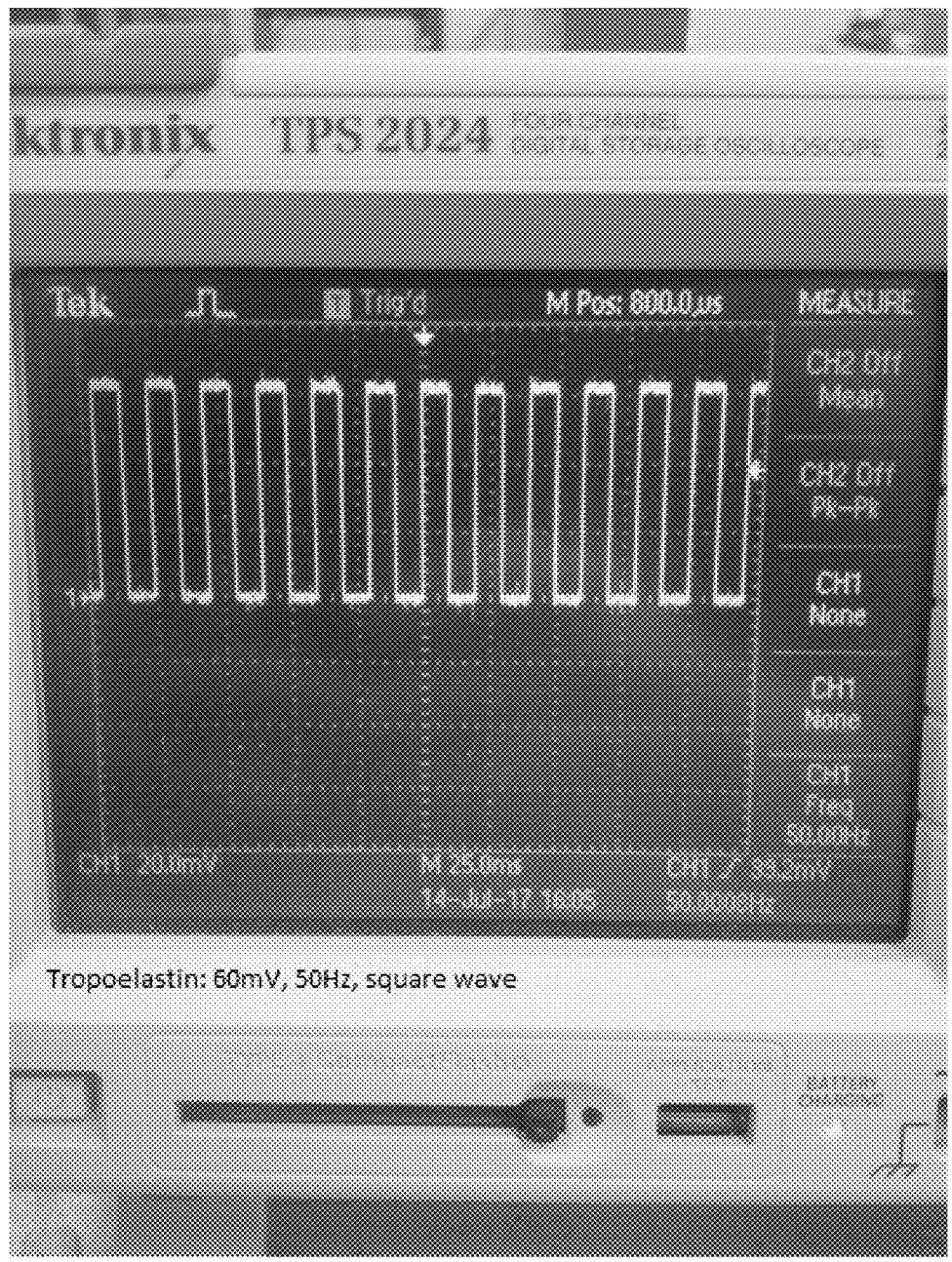
FIG. 13 depicts an image of the signal (voltage and frequency) associated with tropoelastin: 60 mV, 50 Hz, square wave.

In addition to being programmed to produce Klotho, a preferred bioelectric stimulator for treating a subject's kidney(s) is programmed to produce bioelectric signals in the following order: 1. SDF-1 (see, e.g., FIGS. 11 and 12; a stem cell homing factor—recruits a person's own stem cells); 2. VEGF (see, e.g., FIG. 7; for new blood vessel growth); 3. IGF-1 (see, e.g., FIG. 6; for DNA repair at the level of the nucleus); 4. Follistatin (see, e.g., FIG. 5; for muscle and tissue regeneration); 5. RANKL (see, e.g., FIG. 8; for demineralization and tissue loosening when needed); 6. Hepatocyte Growth Factor (see, e.g., FIG. 9; tissue regeneration); 7. eNOS (for dilating blood vessels for increasing flow—e.g., using a bioelectric signal includes (within 15%): alternating high-frequency (HF) and medium-frequency signals (MF), symmetric, biphasic, trapezoid pulses, with 400-μs pulse duration and 1.5/1-s ramp-up/ramp-down duration, respectively). 8. Tropoelastin (see, e.g., FIG. 13; increases elasticity of any tissues such as skin, arteries, aorta, heart and promotes healing of wounds); 9. Activin A+B (see, e.g., FIG. 10); and 10. EGF (for regeneration, using, e.g., 10 V/cm (5 V here), 500 Hz, pulse width 180 μs, square wave). These bioelectric signals are applied subsequent to the Klotho bioelectric signals.

REFERENCES (The Contents of the Entirety of each of which is Incorporated herein by this Reference.)

Brüggemann AK "Effects of Neuromuscular Electrical Stimulation During Hemodialysis on Peripheral Muscle Strength and Exercise Capacity: A Randomized Clinical Trial" Arch Phys Med Rehabil. 2017 May; 98(5):822-831.e1. doi: 10.1016/j.apmr.2016.12.009. Epub 2017 Jan. 16.

Columbia "Implant Procedure Concepts—Pacemaker, ICD and CRT Overview," columbia.edu/itc/hs/medical/hickey/docs/Pacemaker,%20ICD%20and%20CRT%20Overview%20022007.pdf. Prochazka et al. "Cocktail of Factors from Fat-derived Stem Cells Shows Promise for Critical Limb Ischemia" http://www.sciencenewsline.com/news/2016012204520017.html (Jan. 21, 2016).

Di Iorio et al. "High-frequency external muscle stimulation in acute kidney injury (AKI): potential shortening of its clinical course" Clin Nephrol. 2013 January; 79 Suppl 1:S37-45.

Hopkins Medicine "Overview of Pacemakers and Implantable Cardioverter Defibrillators (ICDs),"hopkinsmedicine.org/healthlibrary/conditions/cardiovascular diseases/overview_of_pacemakers_and_implantable_cardioverter_defibrillators_icds_85,P00234/.

Salcedo et al. "Low current electrical stimulation upregulates cytokine expression in the anal sphincter," Int. J. Colorectal Dis., 2012 February; 27(2):221-5. doi: 10.1007/s00384-011-1324-3. Epub (October 2011).

Schardong et al. (2017) "Effects of Intradialytic Neuromuscular Electrical Stimulation on Strength and Muscle Architecture in Patients With Chronic Kidney Failure: Randomized Clinical Trial," Artif Organs. 2017 November; 41(11):1049-1058. doi: 10.1111/aor.12886. Epub 2017 Jun. 16.

Schardong et al. (2018) "Intradialytic neuromuscular electrical stimulation reduces DNA damage in chronic kidney failure patients: a randomized controlled trial," Biomarkers, 23:5, 495-501, DOI: 10.1080/1354750X.2018.1452049.

Takenaka et al. "Klotho protein supplementation reduces blood pressure and renal hypertrophy in db/db mice, a model of type 2 diabetes" Acta Physiol (Oxf). 2019 February; 225(2):e13190. doi: 10.1111/apha.13190. Epub 2018 Oct. 16.

What is claimed is:

1. A method of treating a subject's kidney(s), the method comprising:
   stimulating muscle(s) of the subject for 30 minutes with a bioelectric stimulator programmed to produce and producing a bioelectric signal, which bioelectric signal stimulates said muscle(s) to increase expression and/or release of Klotho polypeptide so as to treat the kidney(s), wherein the bioelectric signal comprises:
   a biphasic pulse at (within 15%) 20 Hz, 0.1 V, and a 7.8 ms pulse duration.

2. The method according to claim 1, wherein the stimulation takes place twice a week.

3. The method according to claim 1, wherein the muscle(s) include(s) at least a quadratus lumborum of the subject.

4. The method according to claim 1, wherein the bioelectric stimulator is further programmed to produce and produces a bioelectric signal of 30 pulses per second with a voltage of (within 15%) 3.5 mV, square wave of 700 to 1500 picoamps.

5. The method according to claim 1, wherein the bioelectric stimulator is further programmed to produce and produces a bioelectric signal of (within 15%) 0.25 mA, pulse duration of 40 pulses per second, pulse width of 100 μs, and frequency of 100 Hz, each signal.

6. The method according to claim 1, wherein the bioelectric stimulator is further programmed to produce and produces a bioelectric signal of (within 15%) 100 mV, 50 Hz, square wave.

7. The method according to claim 1, wherein the bioelectric stimulator is further programmed to produce and produces a bioelectric signal of (within 15%) 3 mV with frequency of 22 Hz, and current of between 1 mA and 3 mA.

8. The method according to claim 1, wherein the bioelectric stimulator is further programmed to produce and produces a bioelectric signal of (within 15%) 3.0 mV, 2 Hz, square wave, alternating frequency with a current of 3 mA.

9. The method according to claim 8, wherein the bioelectric stimulator is further programmed to produce and produces a bioelectric signal of (within 15%) 15 Hz, one (1) Gauss EM field, consisting of 5-millisecond bursts with 5-microsecond pulses followed by 200-μs pulse duration at 30 Hz and with current amplitude of 140 mA.

10. The method according to claim 1, wherein the bioelectric stimulator is further programmed to produce and produces a bioelectric signal of (within 15%): 3.5 V stimulation in 10 second bursts, one (1) burst every 30 seconds at a frequency of about 50 Hz (duration 5 minutes) (wherein the bioelectric signal may be measured three (3) mm deep into tissue).

11. The method according to claim 1, wherein the bioelectric stimulator is further programmed to produce and produces a bioelectric signal including (within 15%): alternating high-frequency and medium-frequency signals, symmetric, biphasic, trapezoid pulses, with 400-μs pulse duration and 1.5/1-s ramp-up/ramp-down duration, respectively (wherein the bioelectric signal may be measured three (3) mm deep into tissue).

12. The method according to claim 1, wherein the bioelectric stimulator is further programmed to produce and produces a bioelectric signal of (within 15%) 0.06 V with 50 Hz alternating electrical field and electric current of 1 mA.

13. The method according to claim 1, wherein the bioelectric stimulator is further programmed to produce and produces a bioelectric signal of (within 15%) 6 mV at 150 Hz monophasic square wave pulse 0.1 ms.

14. The method according to claim 1, wherein the bioelectric stimulator is further programmed to produce and produces a bioelectric signal of (within 15%) 10 V/cm, 500 Hz, pulse width 180 μs, square wave.

15. The method according to claim 1, wherein the bioelectric stimulation is administered to the muscle(s) subject wirelessly.

16. The method according to claim 1, wherein the bioelectric stimulation is administered to the muscle(s) via a gel tape electrode applied to the subject's skin proximate the muscle(s).

17. The method according to claim 16, wherein the gel tape electrode is applied to at least one thigh of the subject.

18. The method according to claim 1, wherein the subject has been diagnosed as having kidney failure, diabetes, aging, and/or cancer.

* * * * *